United States Patent
Kasvikis

(10) Patent No.: US 8,353,436 B2
(45) Date of Patent: Jan. 15, 2013

(54) PIN LOCKING MECHANISM FOR A SURGICAL INSTRUMENT

(75) Inventor: Dino Kasvikis, Middletown, CT (US)

(73) Assignee: Covidien LP, Mansfield, MA (US)

( * ) Notice: Subject to any disclaimer, the term of this patent is extended or adjusted under 35 U.S.C. 154(b) by 282 days.

(21) Appl. No.: 12/754,022

(22) Filed: Apr. 5, 2010

(65) Prior Publication Data

US 2010/0282820 A1    Nov. 11, 2010

Related U.S. Application Data

(60) Provisional application No. 61/175,820, filed on May 6, 2009.

(51) Int. Cl.
*A61B 17/068* (2006.01)

(52) U.S. Cl. ............... 227/175.1; 227/19; 227/175.2; 227/176.1

(58) Field of Classification Search ............ 227/19, 227/176.1, 175.1, 180.1, 175.2, 175.3
See application file for complete search history.

(56) References Cited

U.S. PATENT DOCUMENTS

| | | |
|---|---|---|
| 2,891,250 A | 6/1959 | Fagge |
| 3,080,564 A | 3/1963 | Strekopitov et al. |
| 3,252,643 A | 5/1966 | Strekopitov et al. |
| 3,269,630 A | 8/1966 | Fleischer |
| 3,275,211 A | 9/1966 | Hirsch et al. |
| 3,315,863 A | 4/1967 | O'Dea |
| 3,494,533 A | 2/1970 | Green et al. |
| 3,589,589 A | 6/1971 | Akopov |
| 3,692,224 A | 9/1972 | Astafiev et al. |
| 3,795,034 A | 3/1974 | Strekopytov et al. |
| 3,822,818 A | 7/1974 | Strekopytov et al. |
| 3,935,981 A | 2/1976 | Akopov et al. |
| 3,949,923 A | 4/1976 | Akopov et al. |
| 4,047,654 A | 9/1977 | Alvarado |
| 4,216,891 A | 8/1980 | Behlke |
| 4,244,372 A | 1/1981 | Kapitanov et al. |
| 4,296,881 A | 10/1981 | Lee |
| 4,305,539 A | 12/1981 | Korolkov et al. |
| 4,354,628 A | 10/1982 | Green |
| 4,378,901 A | 4/1983 | Akopov et al. |
| 4,383,634 A | 5/1983 | Green |
| 4,402,444 A | 9/1983 | Green |
| 4,415,112 A | 11/1983 | Green |
| D273,513 S | 4/1984 | Spreckelmeier |
| 4,442,964 A | 4/1984 | Becht |
| 4,470,533 A | 9/1984 | Schuler |
| 4,475,679 A | 10/1984 | Fleury, Jr. |
| 4,485,811 A | 12/1984 | Chernousov et al. |
| 4,506,670 A | 3/1985 | Crossley |
| 4,506,671 A | 3/1985 | Green |
| 4,508,253 A | 4/1985 | Green |
| 4,522,327 A | 6/1985 | Korthoff et al. |

(Continued)

*Primary Examiner* — Scott A. Smith

(57) ABSTRACT

A surgical instrument having a handle portion, an elongated portion defining a longitudinal axis therethrough, an end effector, and a pin. The elongated portion extends distally from the handle portion. The end effector is disposed adjacent the elongated portion and includes a first jaw member and a second jaw member. The pin is disposed in mechanical cooperation with the first jaw member and includes an engaging section. In operation, the pin moves between a first position and a second position. While in the first position, the engaging portion of the pin is spaced from the second jaw member. In the second position, the engaging portion of the pin engages the second jaw member. The second jaw member includes a locking structure configured to maintain the position of the second jaw member with respect to the first jaw member during actuation of the end effector.

4 Claims, 20 Drawing Sheets

U.S. PATENT DOCUMENTS

| | | |
|---|---|---|
| 4,527,724 A | 7/1985 | Chow et al. |
| 4,530,453 A | 7/1985 | Green |
| 4,550,870 A | 11/1985 | Krumme et al. |
| 4,566,620 A | 1/1986 | Green et al. |
| 4,568,009 A | 2/1986 | Green |
| 4,573,622 A | 3/1986 | Green et al. |
| 4,580,712 A | 4/1986 | Green |
| 4,585,153 A | 4/1986 | Failla et al. |
| 4,589,582 A | 5/1986 | Bilotti |
| 4,602,634 A | 7/1986 | Barkley |
| 4,605,001 A | 8/1986 | Rothfuss et al. |
| 4,605,004 A | 8/1986 | DiGiovanni et al. |
| 4,606,344 A | 8/1986 | DiGiovanni |
| 4,606,345 A | 8/1986 | Dorband et al. |
| 4,607,636 A | 8/1986 | Kula et al. |
| 4,612,933 A | 9/1986 | Brinkerhoff et al. |
| 4,617,928 A | 10/1986 | Alfranca |
| 4,632,290 A | 12/1986 | Green et al. |
| 4,665,916 A | 5/1987 | Green |
| 4,684,051 A | 8/1987 | Akopov et al. |
| 4,714,187 A | 12/1987 | Green |
| 4,715,520 A | 12/1987 | Roehr, Jr. et al. |
| 4,728,020 A | 3/1988 | Green et al. |
| 4,767,044 A | 8/1988 | Green |
| 4,788,978 A | 12/1988 | Strekopytov et al. |
| 4,802,614 A | 2/1989 | Green et al. |
| 4,805,823 A | 2/1989 | Rothfuss |
| 4,819,853 A | 4/1989 | Green |
| 4,848,637 A | 7/1989 | Pruitt |
| 4,869,414 A | 9/1989 | Green et al. |
| 4,881,544 A | 11/1989 | Green et al. |
| 4,881,545 A | 11/1989 | Isaacs et al. |
| 4,915,100 A | 4/1990 | Green |
| 4,930,503 A | 6/1990 | Pruitt |
| 4,938,408 A | 7/1990 | Bedi et al. |
| 4,941,623 A | 7/1990 | Pruitt |
| 4,951,861 A | 8/1990 | Schulze et al. |
| 4,964,559 A | 10/1990 | Deniega et al. |
| 5,005,754 A | 4/1991 | Van Overloop |
| 5,018,657 A | 5/1991 | Pedlick et al. |
| 5,071,052 A | 12/1991 | Rodak et al. |
| 5,100,042 A | 3/1992 | Gravener et al. |
| 5,116,349 A | 5/1992 | Aranyi |
| 5,137,198 A | 8/1992 | Nobis et al. |
| 5,172,845 A | 12/1992 | Tejeiro |
| 5,190,203 A | 3/1993 | Rodak |
| 5,219,111 A | 6/1993 | Bilotti et al. |
| 5,240,163 A | 8/1993 | Stein et al. |
| 5,344,060 A | 9/1994 | Gravener et al. |
| 5,368,599 A | 11/1994 | Hirsch et al. |
| 5,405,073 A | 4/1995 | Porter |
| 5,413,267 A | 5/1995 | Solyntjes et al. |
| 5,439,155 A | 8/1995 | Viola |
| 5,452,836 A | 9/1995 | Huitema et al. |
| 5,458,279 A | 10/1995 | Plyley |
| 5,462,215 A | 10/1995 | Viola et al. |
| 5,464,144 A | 11/1995 | Guy et al. |
| 5,465,894 A | 11/1995 | Clark et al. |
| 5,470,006 A | 11/1995 | Rodak |
| 5,470,008 A | 11/1995 | Rodak |
| 5,470,009 A | 11/1995 | Rodak |
| 5,497,934 A | 3/1996 | Brady et al. |
| 5,503,320 A | 4/1996 | Webster et al. |
| 5,509,596 A | 4/1996 | Green et al. |
| 5,542,594 A | 8/1996 | McKean et al. |
| 5,547,117 A | 8/1996 | Hamblin et al. |
| 5,558,266 A | 9/1996 | Green et al. |
| 5,579,978 A | 12/1996 | Green et al. |
| 5,580,067 A | 12/1996 | Hamblin et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,615,820 A | 4/1997 | Viola |
| 5,641,111 A | 6/1997 | Ahrens et al. |
| 5,678,748 A | 10/1997 | Plyley et al. |
| 5,697,543 A | 12/1997 | Burdorff |
| 5,706,997 A | 1/1998 | Green et al. |
| 5,706,998 A | 1/1998 | Plyley et al. |
| 5,732,871 A | 3/1998 | Clark et al. |
| 5,735,445 A | 4/1998 | Vidal et al. |
| 5,772,099 A | 6/1998 | Gravener |
| 5,794,834 A | 8/1998 | Hamblin et al. |
| 5,810,240 A | 9/1998 | Robertson |
| 5,855,311 A | 1/1999 | Hamblin et al. |
| 5,878,937 A | 3/1999 | Green et al. |
| 5,893,506 A | 4/1999 | Powell |
| 5,894,979 A | 4/1999 | Powell |
| 5,964,394 A | 10/1999 | Robertson |
| 6,045,560 A | 4/2000 | McKean et al. |
| 6,638,285 B2 | 10/2003 | Gabbay |
| 6,805,273 B2 | 10/2004 | Bilotti et al. |
| 6,817,508 B1 | 11/2004 | Racenet et al. |
| 6,988,650 B2 | 1/2006 | Schwemberger et al. |
| 7,070,083 B2 | 7/2006 | Jankowski |
| 7,134,587 B2 | 11/2006 | Schwemberger et al. |
| 7,147,139 B2 | 12/2006 | Schwemberger et al. |
| 7,147,140 B2 | 12/2006 | Wukusick et al. |
| 7,204,404 B2 | 4/2007 | Nguyen et al. |
| 7,207,472 B2 | 4/2007 | Wukusick et al. |
| 7,210,609 B2 | 5/2007 | Leiboff et |
| 7,237,708 B1 | 7/2007 | Guy et al. |
| 7,275,674 B2 | 10/2007 | Racenet et al. |
| RE40,237 E | 4/2008 | Bilotti et al. |
| 7,407,076 B2 | 8/2008 | Racenet et al. |
| 7,431,190 B2 | 10/2008 | Hoffman |
| 7,522,854 B2 | 4/2009 | Kinouchi et al. |
| 7,549,563 B2 | 6/2009 | Mather et al. |
| 7,568,605 B2 | 8/2009 | Kruszynski |
| 7,641,092 B2 | 1/2010 | Kruszynski et al. |
| 7,988,028 B2 * | 8/2011 | Farascioni et al. ......... 227/180.1 |
| 8,033,439 B2 * | 10/2011 | Racenet et al. ............ 227/176.1 |
| 8,136,712 B2 * | 3/2012 | Zingman .................... 227/179.1 |
| 2004/0084505 A1 | 5/2004 | Bilotti et al. |
| 2004/0164123 A1 | 8/2004 | Racenet et al. |
| 2005/0247752 A1 | 11/2005 | Kelly et al. |
| 2005/0247753 A1 | 11/2005 | Kelly et al. |
| 2006/0163312 A1 | 7/2006 | Viola et al. |
| 2006/0201992 A1 | 9/2006 | Racenet et al. |
| 2006/0273135 A1 | 12/2006 | Beetel et al. |
| 2007/0029364 A1 | 2/2007 | Kruszynski et al. |
| 2007/0039996 A1 | 2/2007 | Mather et al. |
| 2007/0039997 A1 | 2/2007 | Mather et al. |
| 2007/0095877 A1 | 5/2007 | Racenet et al. |
| 2007/0187456 A1 | 8/2007 | Viola et al. |
| 2007/0221702 A1 | 9/2007 | Kruszynski |
| 2007/0262116 A1 | 11/2007 | Hueil |
| 2008/0023523 A1 | 1/2008 | Racenet et al. |
| 2008/0093415 A1 | 4/2008 | Bilotti |
| 2009/0255976 A1 | 10/2009 | Marczyk et al. |
| 2009/0261143 A1 | 10/2009 | Wixey et al. |
| 2009/0277948 A1 | 11/2009 | Beardsley et al. |
| 2009/0302092 A1 | 12/2009 | Kasvikis et al. |
| 2009/0302093 A1 | 12/2009 | Kasvikis |
| 2010/0038403 A1 | 2/2010 | D'Arcangelo |
| 2010/0048988 A1 | 2/2010 | Pastorelli et al. |

\* cited by examiner

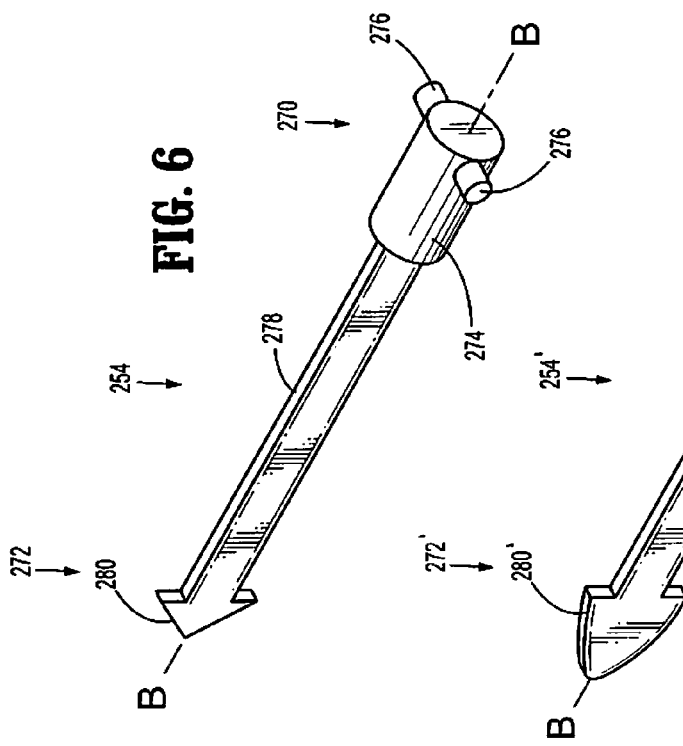
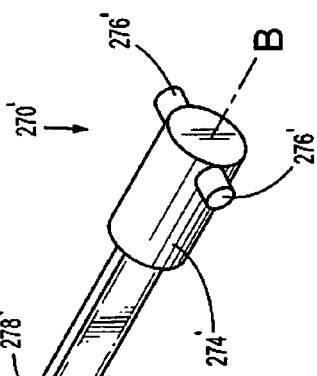
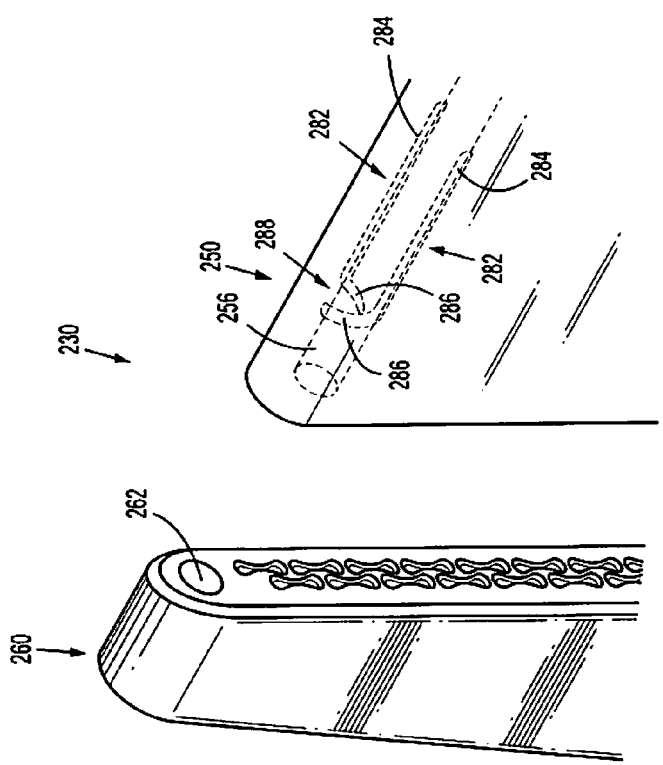
FIG. 6
FIG. 6A
FIG. 5

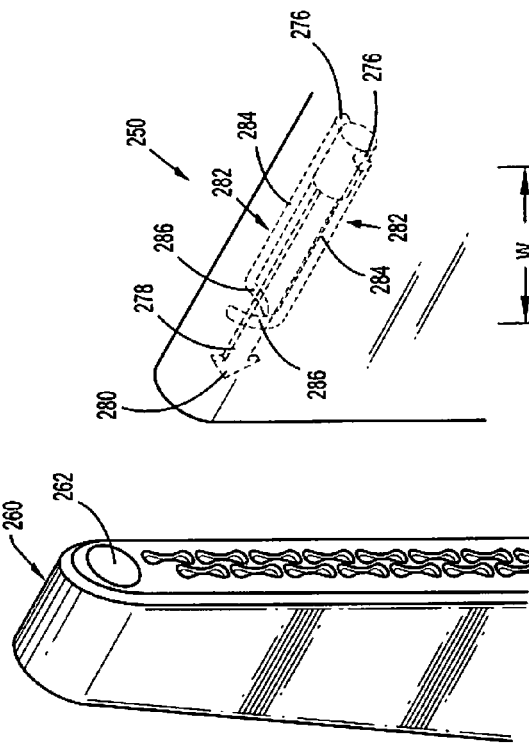
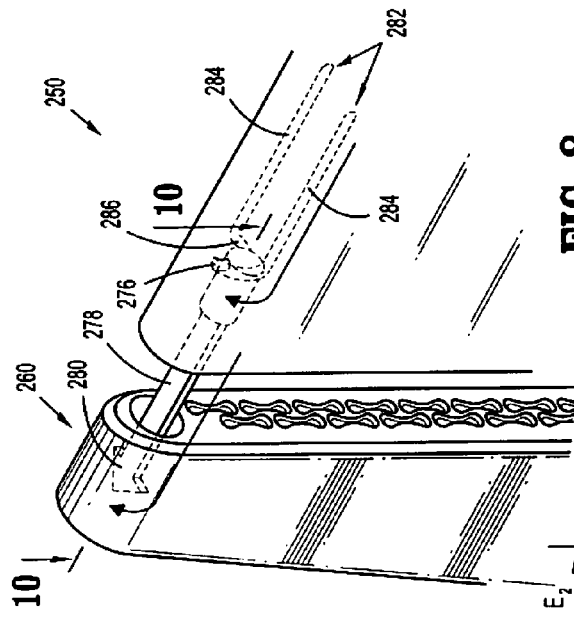
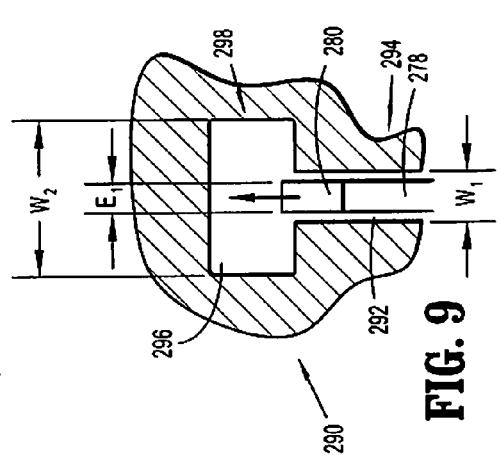
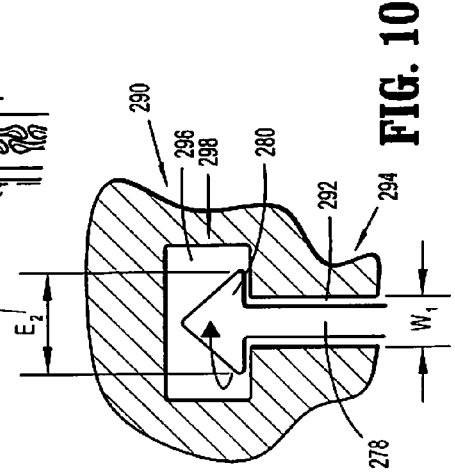
FIG. 7
FIG. 8
FIG. 9
FIG. 10

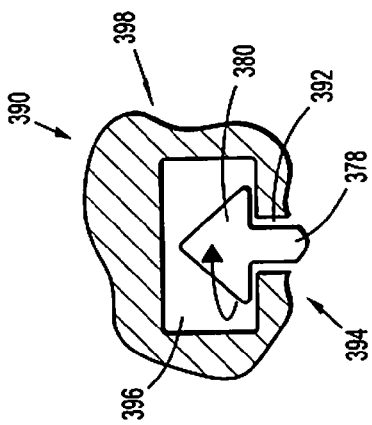
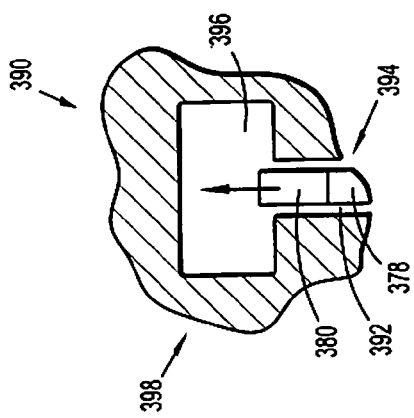
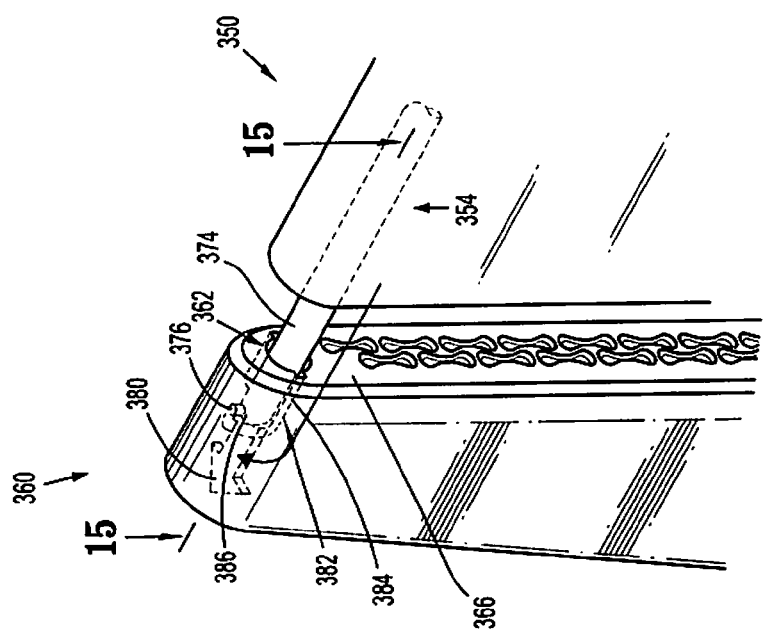

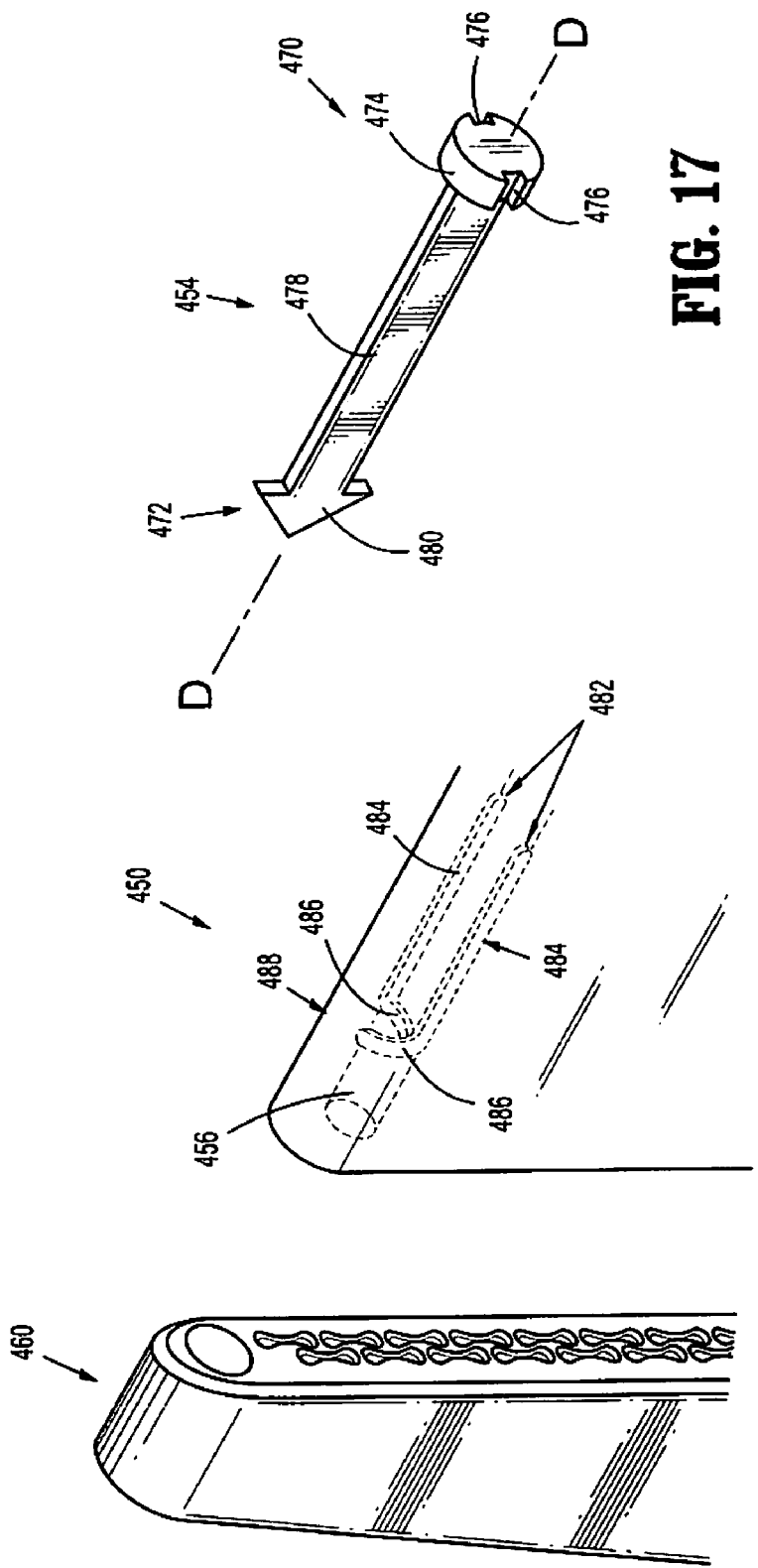

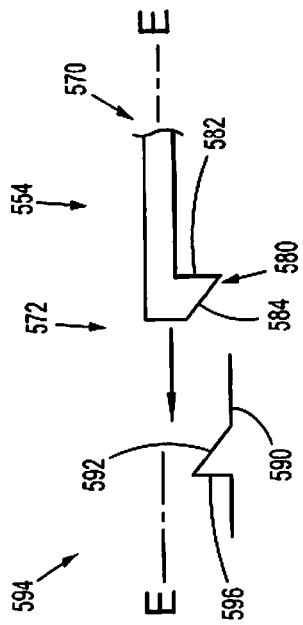
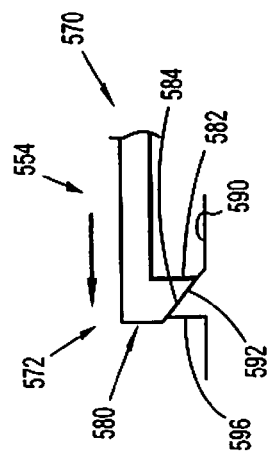
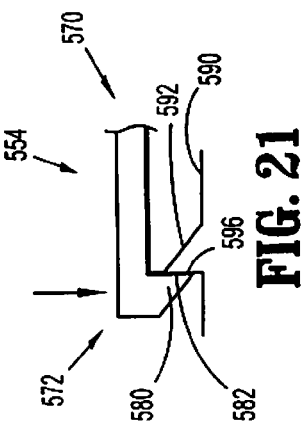
FIG. 19    FIG. 20    FIG. 21
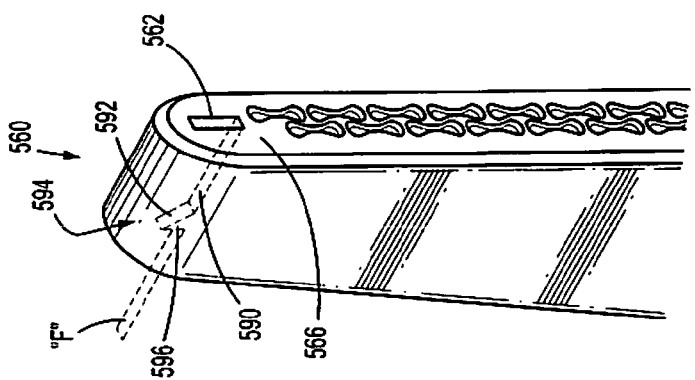
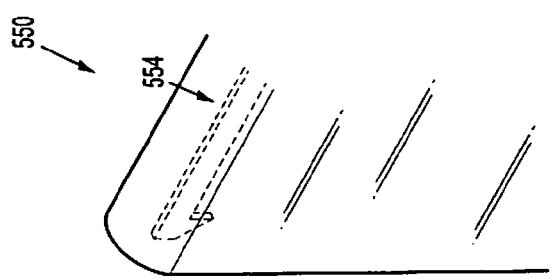
FIG. 18

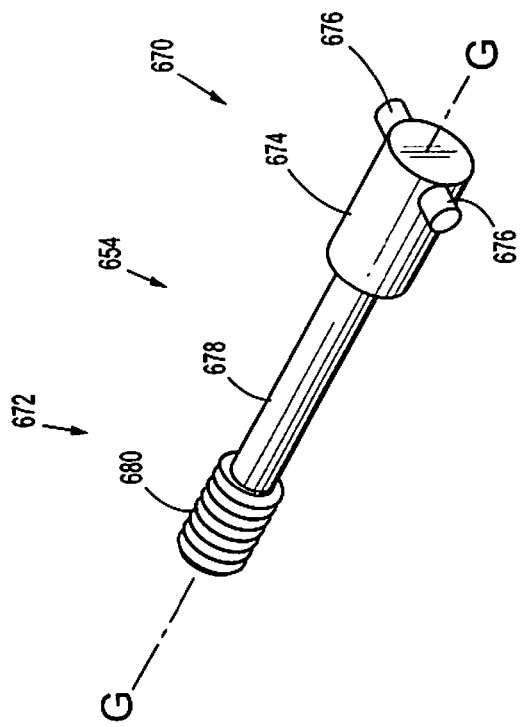
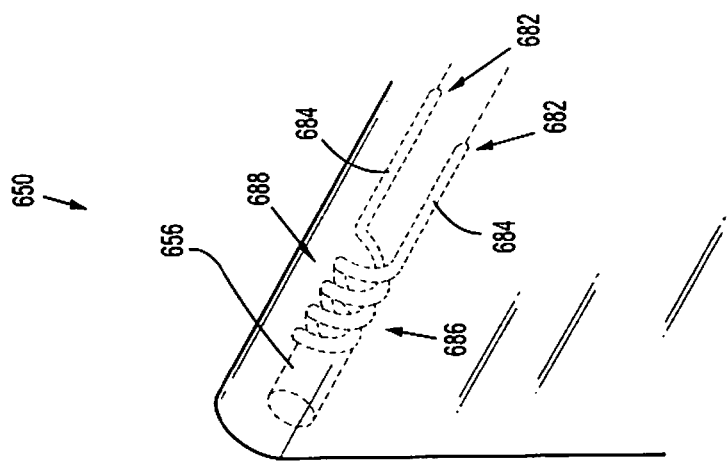
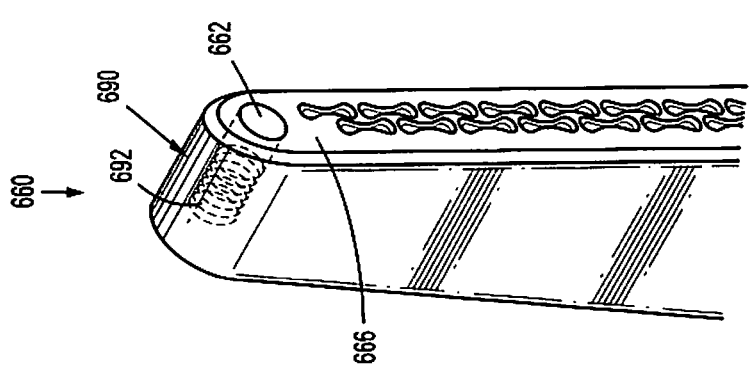

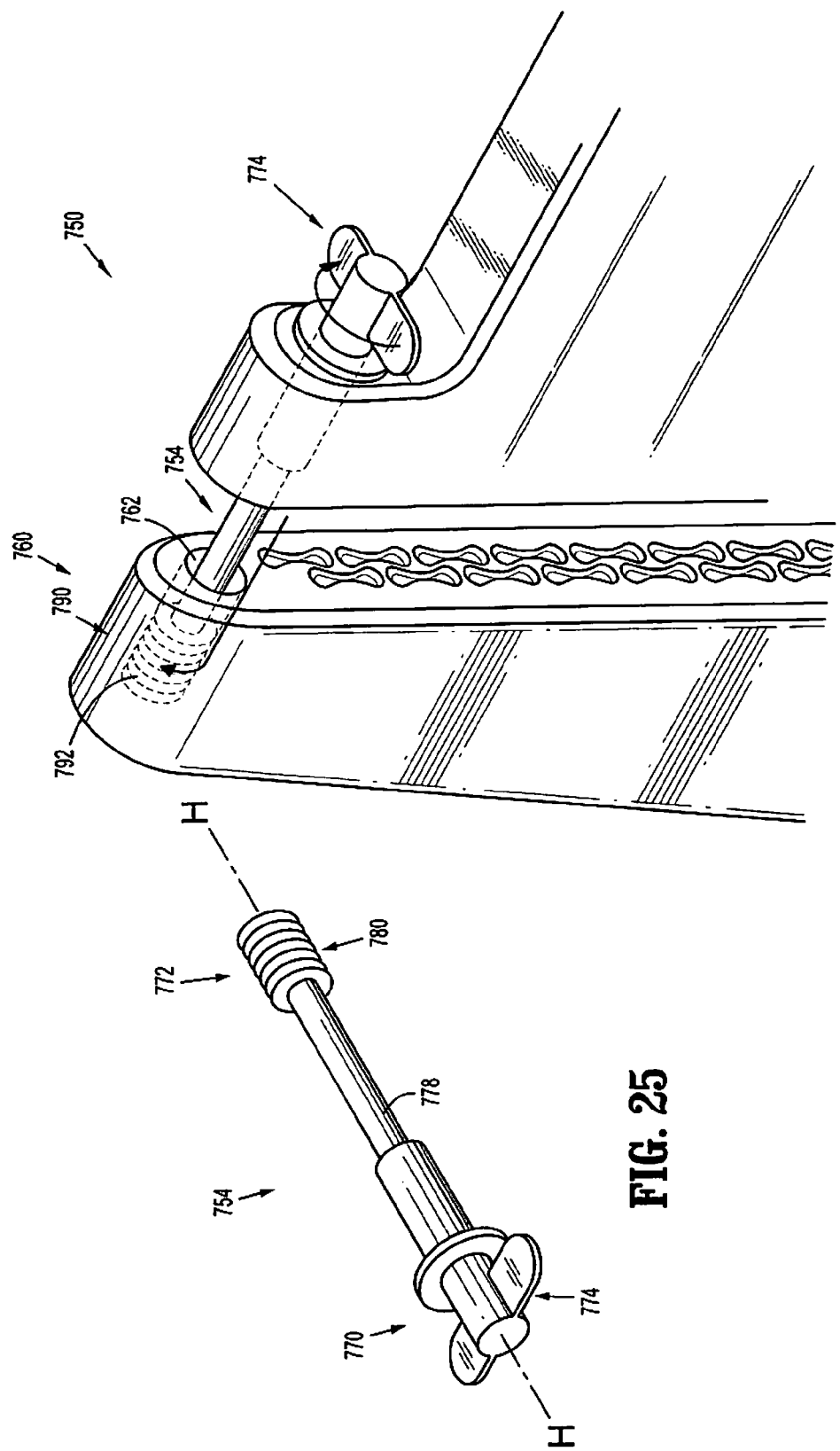

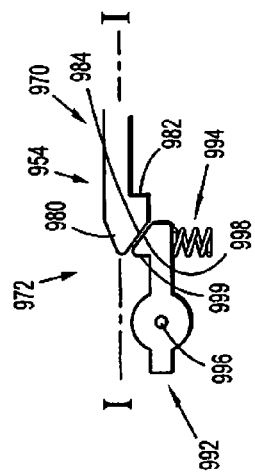
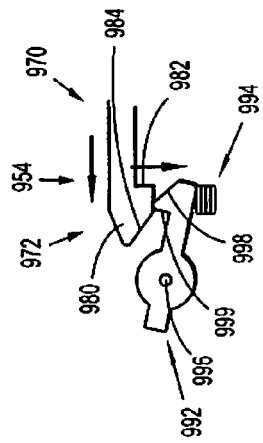
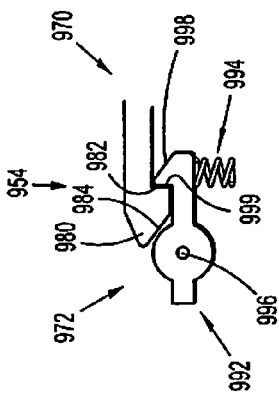
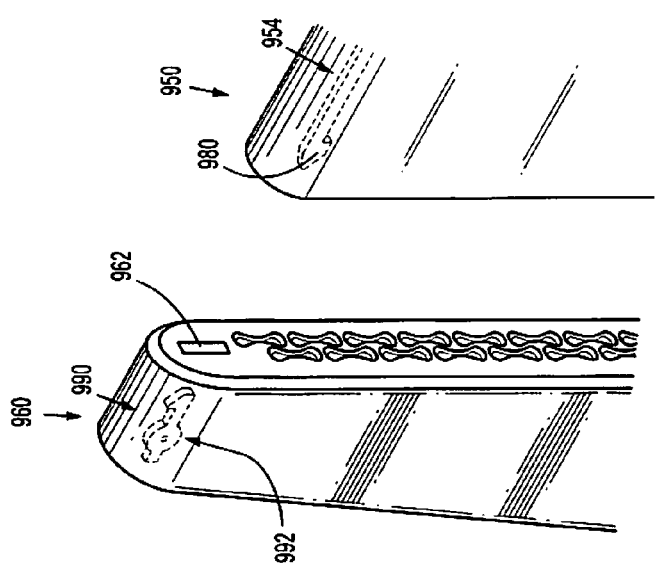

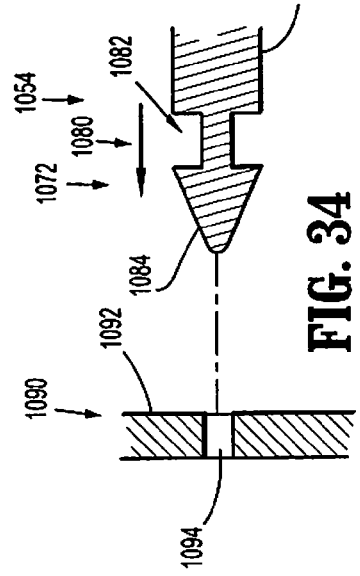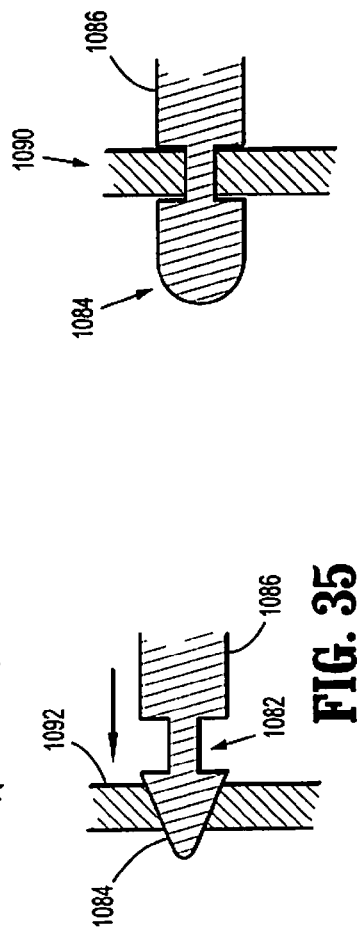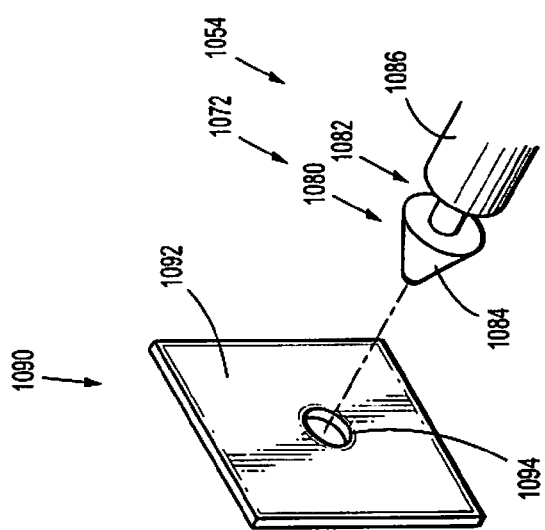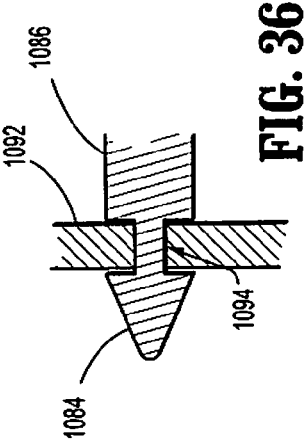

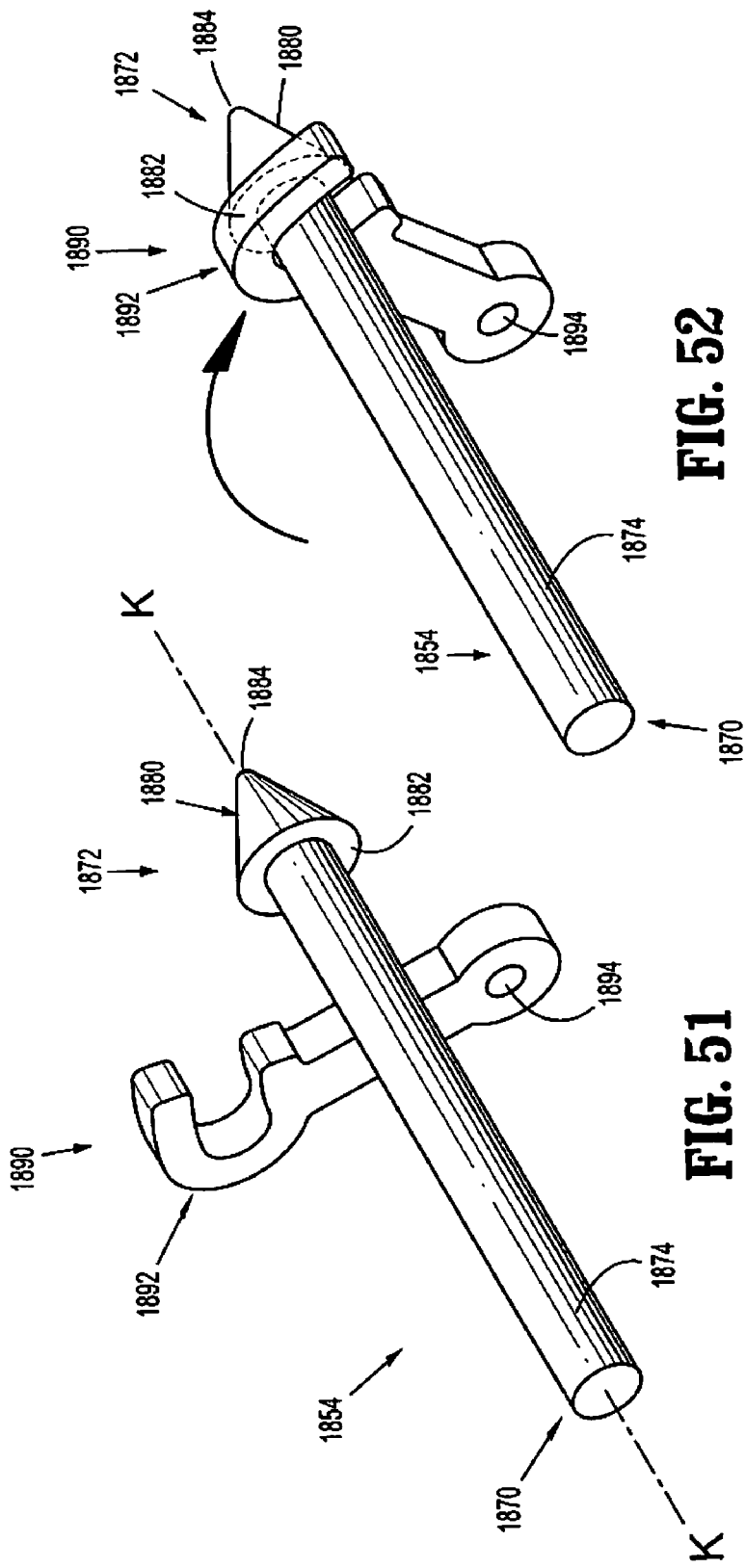

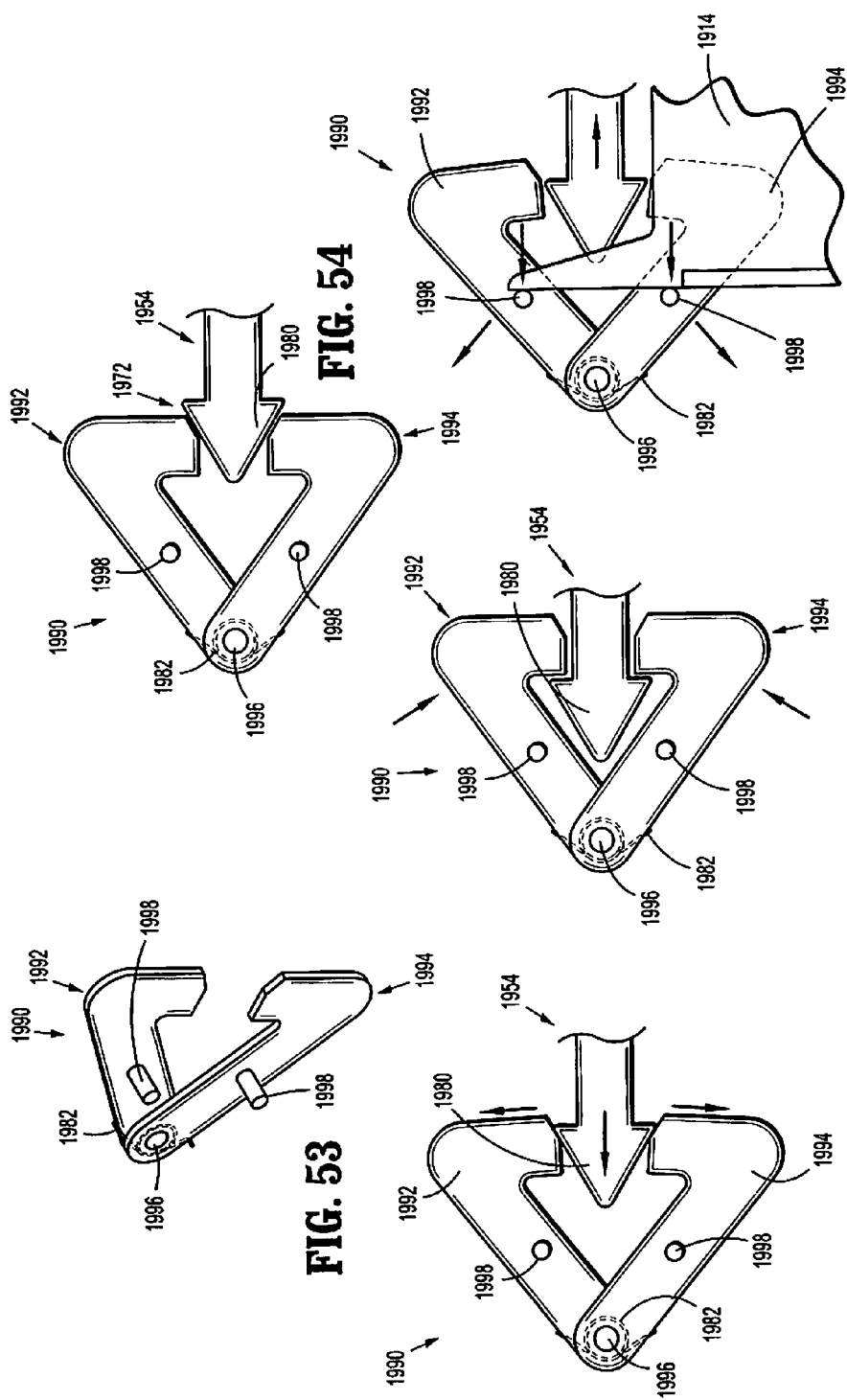

PIN LOCKING MECHANISM FOR A SURGICAL INSTRUMENT

This application claims priority to provisional application Ser. No. 61/175,820, filed May 6, 2009, the entire contents of which are incorporated herein by reference.

BACKGROUND

1. Technical Field

The present disclosure relates generally to a surgical instrument and, more specifically, to a surgical instrument for clamping and joining tissue.

2. Background of Related Art

Certain surgical stapling instruments are used for applying rows of staples through compressed living tissue. These surgical stapling instruments are employed, for example, for fastening tissue or organs prior to transection or resection or during anastomoses. In some cases, these surgical stapling instruments are utilized for occluding organs in thoracic and abdominal procedures.

Typically, such surgical stapling instruments include an anvil assembly, a cartridge assembly for supporting an array of surgical staples, an approximation mechanism for approximating the cartridge and anvil assemblies, an alignment or guide pin assembly for capturing tissue between the cartridge and anvil assemblies and for maintaining alignment between the cartridge and anvil assemblies during approximation and firing, and a firing mechanism for ejecting the surgical staples from the cartridge assembly.

In use, the alignment pin assembly is advanced and the anvil and cartridge assemblies are approximated. Next, the surgeon fires the instrument to place staples in tissue. Optionally, the surgeon may use the same instrument or a separate device to cut the tissue adjacent or between the row(s) of staples. The alignment pin in some instances is advanced automatically with approximation of the cartridge; in other instances it is advanced by a separate mechanism.

It would be advantageous to provide an alignment pin arrangement to enhance engagement between the cartridge and anvil assemblies.

SUMMARY

The present disclosure relates to a surgical instrument having a locking mechanism for securing an alignment pin. The surgical instrument generally includes a handle portion, an elongated portion defining a longitudinal axis therethrough, an end effector, and an alignment pin. The elongated portion extends distally from the handle portion. The end effector is disposed adjacent the distal portion of the elongated portion and includes a first jaw member and a second jaw member. The pin is disposed in mechanical cooperation with the first jaw member and includes an engagement section. In operation, the pin moves between a first position and a second position. While in the first position, the engagement section of the pin is spaced from the second jaw member. In the second position, the engagement section of the pin engages the second jaw member. The second jaw member includes a locking structure configured to maintain the pin in the second position to maintain the position of the second jaw member with respect to the first jaw member during actuation of the end effector.

BRIEF DESCRIPTION OF DRAWINGS

Various embodiments of the presently disclosed surgical stapling instrument are disclosed herein with reference to the drawings, wherein:

FIG. 5 is a perspective view of a first embodiment of an end effector of the present disclosure;

FIG. 6 is a perspective view of a pin for use with the end effector shown in FIG. 5;

FIG. 6A is a perspective view of an alternate embodiment of a pin for use with the end effector shown in FIG. 5;

FIG. 7 is perspective view of the end effector shown in FIG. 5 with the pin depicted in FIG. 6 positioned therein, and showing the pin located in a first or disengaged position;

FIG. 8 is a perspective view of the end effector shown in FIG. 5 with the pin depicted in FIG. 6 positioned therein, and showing the pin located in a second or engaged position.

FIG. 9 is a top cross-sectional view of a locking structure within the end effector illustrated in FIG. 5 and the pin shown in FIG. 6, depicting the pin in a disengaged position;

FIG. 10 is a top cross-sectional view of a locking structure within the end effector shown in FIG. 5 and the pin illustrated in FIG. 6 taken along line 10-10 of FIG. 8, depicting the pin in the engaged position;

FIG. 13 is a perspective view of the portion of the end effector shown in FIG. 11 with the pin depicted in FIG. 12 positioned therein;

FIG. 14 is a top cross-sectional view of the locking structure within the end effector illustrated in FIG. 13, showing the pin located in a disengaged position;

FIG. 15 is a top cross-sectional view of the locking structure within the end effector shown in FIG. 13, taken along line 15-15 of FIG. 13, illustrating the pin located in an engaged position;

FIG. 16 is a perspective view of another embodiment of an end effector;

FIG. 17 is a perspective view of another embodiment of a pin for use with the end effector illustrated in FIG. 16;

FIG. 18 is a perspective view of a further embodiment of an end effector;

FIGS. 19-21 are side views of the pin and a portion of the end effector depicted in FIG. 18 at different stages of operation to illustrate movement of the pin from a disengaged to an engaged position;

FIG. 22 is a perspective view of another embodiment of an end effector;

FIG. 23 is a perspective view of another embodiment of a pin for use with the end effector shown in FIG. 22;

FIG. 25 is a perspective view of yet another embodiment of a pin;

FIG. 26 is a perspective view of an embodiment of an end effector with the pin shown in FIG. 25 positioned in the engaged position;

FIG. 29 is a perspective view of another embodiment of an end effector with a pin positioned therein;

FIGS. 30-32 are side views of the pin and engagement structure of the end effector of FIG. 29 at different stages of operation to illustrate movement of the pin from a disengaged to an engaged position;

FIG. 33 is a perspective view of a sheet of an end effector and an alternate embodiment of a pin;

FIGS. 34-36 are side cross-sectional views of the pin and the sheet of FIG. 33 at different stages of operation to illustrate movement of the pin from a disengaged to an engaged position;

FIG. 37 is a side cross-sectional view of the sheet shown in FIG. 33 and an alternate embodiment of the pin;

FIGS. 51 and 52 are perspective views of an alternate embodiment of a pin and a hook adapted to pivot toward and away from the pin;

FIG. 53 is a perspective view of an alternate embodiment of a locking mechanism for securing a pin, the locking mechanism including first and second arm members;

FIGS. 54-57 are a side views of the locking mechanism shown in FIG. 53 engaging a pin at different stages of operation;

DETAILED DESCRIPTION OF THE EMBODIMENTS

Figure 1:
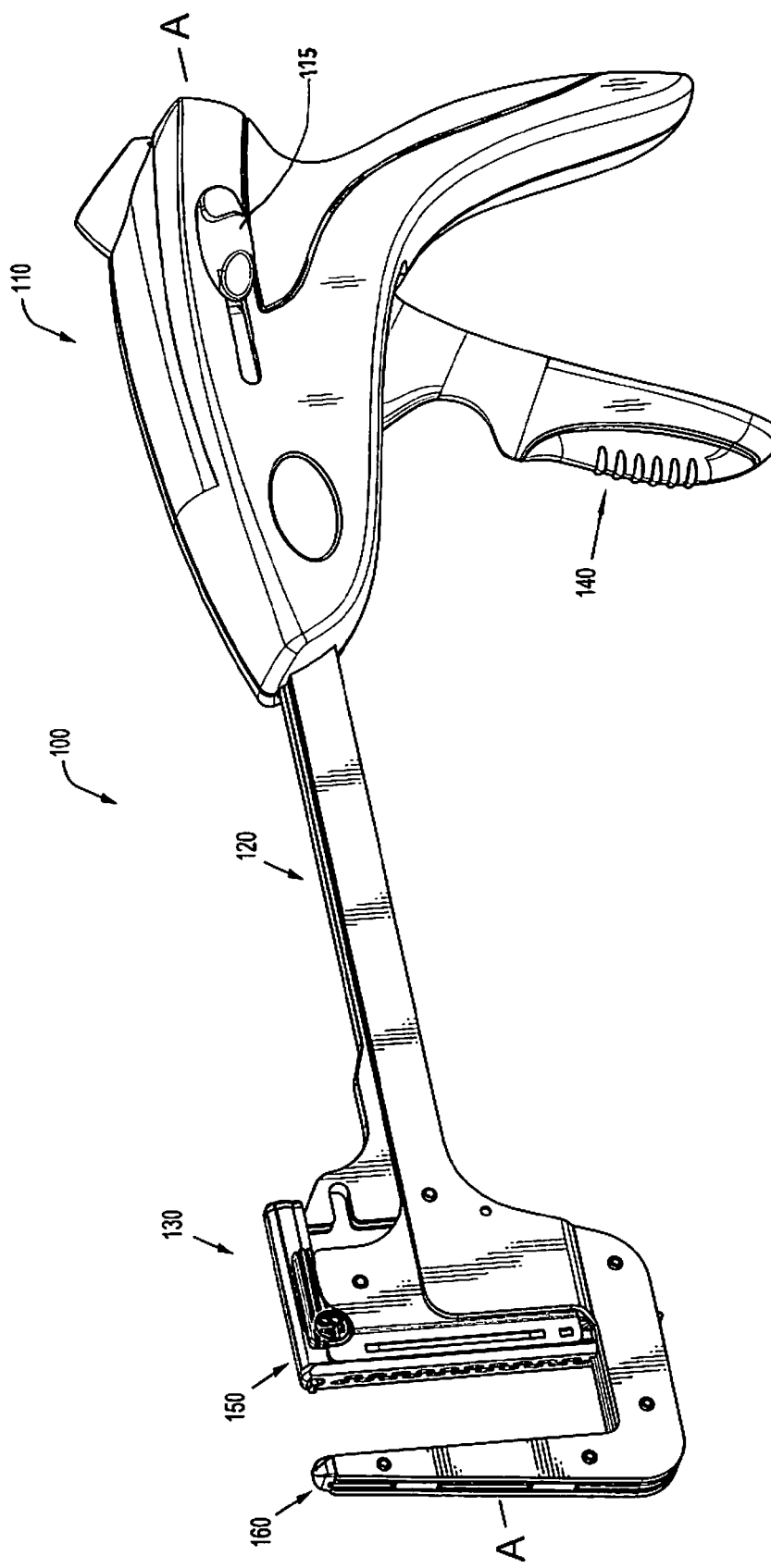
FIG. 1 is a perspective view of a prior art surgical stapling instrument.

Embodiments of the presently disclosed surgical stapling instrument are described in detail with reference to the drawings, wherein like reference numerals designate corresponding elements in each of the several views. In the description that follows, the term "proximal" refers to the end or portion of the surgical stapling instrument closer to the user, whereas the term "distal" refers to the end or portion of the surgical stapling instrument further away from the user.

In the interest of brevity, the present disclosure focuses on pin locking mechanisms for a surgical stapling instrument designated in the drawings by reference numeral 100. U.S. Pat. No. 7,407,076, the entire contents of which are hereby incorporated by reference, describes in detail the structure and operation of an embodiment of surgical stapling instrument 100.

FIG. 1 illustrates a surgical stapling instrument 100 designed for applying fasteners, cutting tissue, or both. In brief, surgical stapling instrument 100 includes a handle portion 110, an elongate portion 120, and an end effector 130 extending from the distal portion of the elongate portion 120. Handle portion 110 contains a trigger 140 for actuating end effector 130. Elongate portion 120 extends distally from handle portion 110 and defines a longitudinal axis A-A therealong. End effector 130 is disposed adjacent to the distal portion of elongate portion 120 and includes a first jaw member or cartridge assembly 150 and a second jaw member or anvil assembly 160. In this embodiment, cartridge assembly 150 is adapted to move longitudinally with respect to anvil assembly 160 upon actuation of trigger 140 to clamp tissue between the jaw members 150, 160. It is also contemplated that the anvil assembly can be moved toward the cartridge or that the cartridge and anvil assemblies can both be moved toward each other to approximate the assemblies and clamp tissue therebetween.

Figure 3:
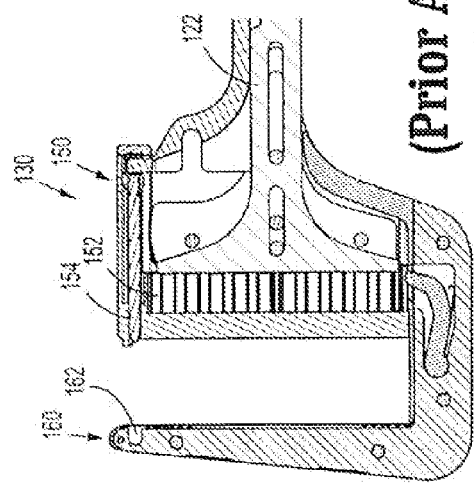
FIG. 3 is side cross-sectional view of the end effector shown in FIG. 2 with the jaw members in the open position.
Figure 2:
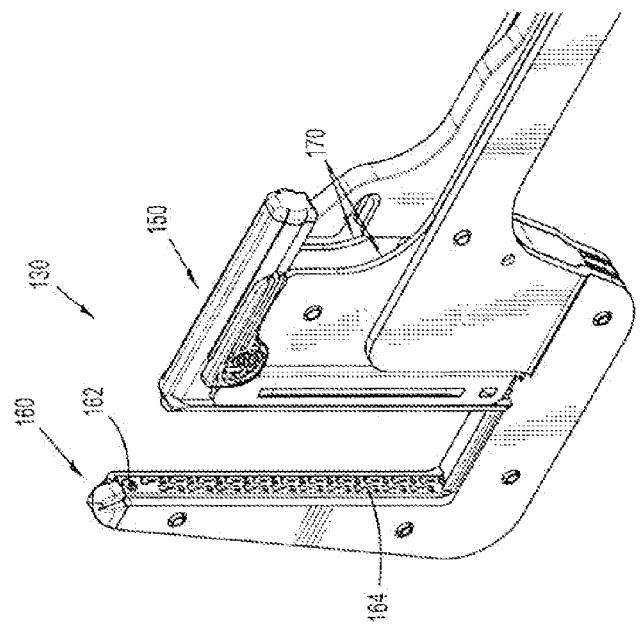
FIG. 2 is a perspective view of an end effector of the surgical stapling instrument shown in FIG. 1.

With reference to FIGS. 2-3, cartridge assembly 150 and anvil assembly 160 of end effector 130 can collectively join tissue. Cartridge assembly 150 includes a plurality of slots 152 each capable of holding a staple or any other suitable fastener. Each slot 152 is operatively associated with a pusher thrust bar or plunger 122. Pusher 122 extends along elongate portion 120 and partially into cartridge assembly 150. Cartridge assembly 150 can optionally include a knife advanceable to cut tissue clamped between the cartridge and anvil assemblies 150, 160, respectively. In use, pusher 122 moves distally upon actuation of trigger 140 (see FIG. 1) and causes the ejection of the staples disposed in slots 152. In addition to slots 152, cartridge assembly 150 includes a pin 154 operatively connected to pusher 122 and a bore 156 dimensioned to slidably receive pin 154. Pin 154 is adapted to move longitudinally along bore 156 in response to a translation of pusher 122. The pin 154 can alternatively be moved by a sliding knob 155 in the handle portion 110. In the embodiment depicted in FIG. 2, anvil assembly 160 has a hole 162 designed to receive at least a portion of pin 154. Anvil assembly 160 has staple-deforming pockets 164 for deforming the fasteners ejected from cartridge assembly 150. An elongated slot can be provided between the rows of pockets 164 in the anvil assembly to accommodate a knife if provided.

Figure 4:
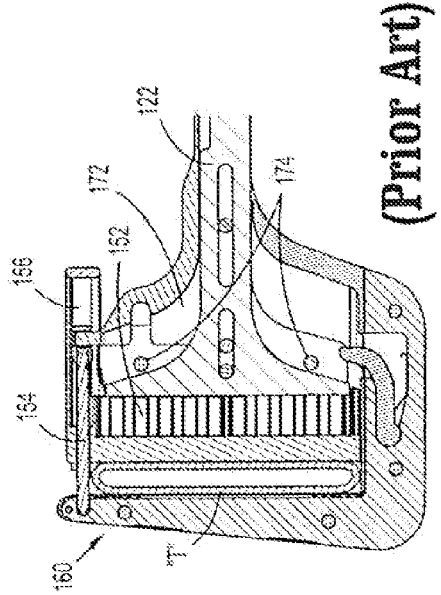
FIG. 4 is a side cross-sectional view of the end effector shown in FIG. 2 with the jaw members in the closed position.

While anvil assembly 160 remains stationary with respect to cartridge assembly 150 during operation, cartridge assembly 150 is movable longitudinally between a proximal position and a distal position upon actuation of trigger 140 (see FIG. 1). In the proximal position, cartridge assembly 150 is spaced apart from anvil assembly 160 as seen in FIG. 3. The actuation of trigger 140 causes clamp slides 170 to move distally which in turn causes thrust bar 122 to move distally due to pins 174. In turn, the distal translation of thrust bar 122 causes the distal movement of cartridge assembly 150 toward anvil assembly 160 to an approximated position. While cartridge assembly 150 moves from the proximal position toward the distal position, end effector 130 clamps any tissue "T" placed between cartridge assembly 150 and anvil assembly 160 as shown in FIG. 4. In the distal position, cartridge assembly 150 is located closer to anvil assembly 160 and presses tissue "T" against anvil assembly 160.

Further actuation of trigger 140, i.e. a second squeeze of the trigger 140, once cartridge assembly 150 is located in the distal (approximated) position, causes ejection of the fasteners positioned in slots 152. That is, the continued distal translation of pusher 122, once cartridge assembly 150 is located in the distal position, causes the deployment of the fasteners positioned in slots 152. During deployment, these fasteners exit slots 152 and advance through tissue and into contact with staple-deforming pockets 164 of anvil assembly 160 for formation thereof into, e.g. a B-shaped configuration. If a knife is provided, actuation of trigger 140 could also advance the knife.

Note the distal motion of clamp slides 170 causes pin 154 to move distally along bore 156 due to the operative connection of the alignment pin pusher 172 to the clamps slides 170 via pins extending through elongated slots in pin pusher 172 as described in the U.S. Pat. No. 7,407,076. Pin pusher 172 includes a vertical portion having an abutment member configured to engage the proximal end of the pin 154. Upon sufficient distal movement, hole 162 of anvil assembly 160 receives a portion of pin 154. The structural interaction between pin 154 and hole 162 (when cartridge assembly 150 is located in the distal position) assists in the alignment of slots 152 with staple-deforming pockets 164. Pin 154 is shown having a substantially cylindrical shape. It should be appreciated that alignment pin 154 can alternatively be moved manually as pin pusher 172 is moved manually, e.g. by sliding knob 115.

Figure 61:
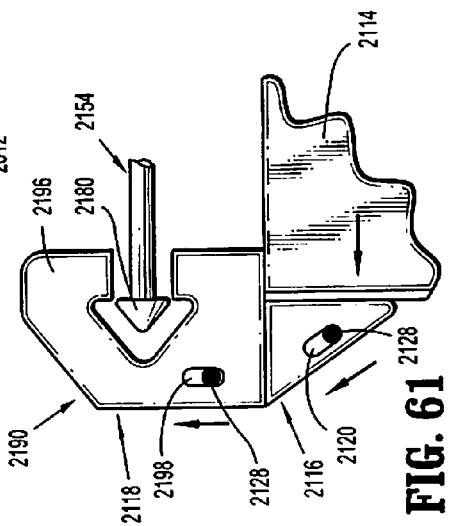
FIGS. 60 and 61 are side views of an alternate embodiment of a pin and an end effector including a sliding cam member for locking the pin to the end effector, illustrating the sliding cam member at different stages of operation.

Turning now to embodiments of the present disclosure, FIGS. 5-61 illustrate various pin/hole structures to enhance pin retention. These structures can be used with the stapler of FIG. 1 described above or with other suitable surgical staplers. They can be configured to move automatically with approximation of the cartridge and/or moved by the user separate from approximation. Note that for brevity, movement of the pins disclosed herein is generally discussed in some embodiments as occurring in response to actuation of the trigger and in other embodiments as being moved selectively movable, e.g. by an independent slidable or other knob. It should be understood, however, that it is contemplated that the pins disclosed herein can be moved in either way or in both ways.

Turning first to FIGS. 5 and 6 illustrating a first embodiment of the locking pin structure of the present disclosure, end effector 230 includes cartridge assembly 250 and anvil assembly 260. Cartridge assembly 250 includes a bore 256 adapted to receive alignment pin 254. Pin 254 includes a proximal portion 270 and a distal portion 272 and defines a longitudinal axis B-B therealong. The proximal portion 270 of pin 254 includes a substantially cylindrical body 274 and a pair of protrusions 276 extending radially from body 274. Pin 254 additionally includes an elongate plate 278 extending distally from body 274. Elongate plate 278 preferably has a substantially planar configuration and extends between proximal portion 270 and distal portion 272 of pin 274. Distal portion 272 of pin 254 includes flat engagement section or head section 280 having a substantially triangular shape in the form of an arrowhead. As discussed in detail below, pin 254 is adapted to advance longitudinally through bore 256 of cartridge assembly 250 upon actuation of trigger 140 (see FIG. 1) or by movement of knob 115.

Pin 278' of FIG. 6A has a spade shaped distal portion 280'. In all other respects, pin 278' is identical to pin 278 of FIG. 6 and for convenience like parts have been labeled with "prime" designations in FIG. 6A.

Cartridge assembly 250 further includes at least one groove 282 formed therein along bore 256 to aid in the longitudinal motion of pin 254. In the embodiment shown in FIG. 5, cartridge assembly 250 features two grooves 282. Each groove 282 is configured to slidably receive a protrusion 276 of pin 272. The geometry of each groove 282 allows pin 254 to slide initially through bore 256 and then rotate to change the orientation or position of engaging section 280 with respect to anvil assembly 260 and cartridge assembly 250. More specifically, each groove 282 includes a longitudinal or straight portion 284 and an arcuate or curved portion 286 located at a distal end 288 thereof. The straight portion 284 of grooves 282 directs the initial longitudinal translation of pin 254 through bore 256, whereas the curved portion 286 guides the rotation of pin 254. As pin 254 moves distally, protrusions 276 slide first along the straight portion 284 of grooves 282. Upon sufficient distal advancement of pin 254, the protrusions 276 eventually slidably engage the curved portion 286 of grooves 282. When protrusions 276 move within the curved portion 286 of grooves 282, pin 254 rotates about longitudinal axis B-B. As pin 254 rotates about longitudinal axis B-B, engagement section 280 changes its position or orientation, thereby securing pin 254 to anvil assembly 260 as discussed in detail below.

FIGS. 7-10 illustrates the operational stages of pin 254 during actuation of the surgical stapling instrument such as instrument 100 of FIG. 1. Pin 254 works along with a locking structure 290 disposed in anvil assembly 260 to minimize or prevent anvil assembly 260 from cantilevering away from cartridge assembly 250 during firing. Hole 262 of anvil assembly 260 leads to locking structure 290. Locking structure 290 includes a slot 292 positioned at a proximal end 294 thereof and a cavity 296 located at distal end 298 thereof. Cavity 296 is disposed in communication with slot 292. Slot 292 is configured to receive engagement section 280 and at least a portion of elongate plate 278 while pin 254 is oriented in a first position as shown in FIG. 9. Cavity 296 can receive engagement section 280 when pin 254 is oriented in either the first position (as seen in FIG. 7) or the second position (as depicted in FIG. 8). When engagement section 280 of pin 254 is positioned inside cavity 296, the geometry of cavity 296 and slot 292 precludes or at least hinders engagement section 280 from escaping anvil assembly 260 if pin 254 is oriented in the second position as shown in FIG. 10.

As illustrated in FIGS. 9 and 10, cavity 296 has a width "$W_2$" greater that the width "$W_1$" of slot 292. Engagement section 280 and elongate plate 278 have substantially similar widths. Width "$E_1$" of engagement section 280 is smaller than width "$W_1$" of slot 292 and "$W_2$" of cavity 296. Engagement section 280 of pin 254 has a dimension "$E_2$" that is larger than width "$W_1$" of slot 292 but smaller than width "$W_2$" of cavity 296. The geometries of cavity 296, slot 292, and engagement section 280 of pin 254 permit engagement section 280 of pin 254 to pass through slot 292 and cavity 296 when pin is positioned in the first position (see FIG. 9), while preventing or at least inhibiting engagement section 280 from escaping anvil assembly 260 when pin 254 is oriented in the second position and engagement section 280 is located inside cavity 296. When pin 254 is oriented in the second position and its engagement section 280 is located within cavity 296, locking structure 290 maintains the position of anvil assembly 260 with respect to cartridge assembly 250 during actuation of end effector 230 (see FIG. 5), thereby impeding or hindering anvil assembly 260 from cantilevering away from cartridge assembly 250.

In operation, when a user actuates trigger 140 (see FIG. 1) to advance the cartridge assembly toward the anvil assembly, pin 254 is advanced distally. As pin 254 moves distally, protrusions 276 initially slide along the straight portion 284 of grooves 282. At this moment, pin 254 translates longitudinally through bore 256. While pin 254 advances in a distal direction, engagement section 280 is oriented in the first position (as seen in FIG. 9) and is therefore capable of passing through slot 292. The continued longitudinal motion of pin 254 through bore 256 drives protrusions 276 toward the curved portion 286 of grooves 282. The length of straight portion 284 allows protrusions 276 to reach the curved portion 386 of grooves 282 just as engagement section 280 enters cavity 296. At this point, pin 254 begins to rotate about longitudinal axis B-B, reorienting engagement section 280 from the first position (as shown in FIG. 9) to the second position (as illustrated in FIG. 10). By the time protrusions 276 slide along the curved portion 286 of grooves 282, engagement portion 280 is already positioned inside cavity 296. Once engagement portion 280 rotates to its second position (illustratively about 180 degree rotation although other rotations are also contemplated), the geometry of cavity 296 and slot 292 blocks engagement portion 280 from exiting anvil assembly 260 (the slot opening being less than the height of portion 280 so engagement section contacts the wall of the slot if retracted), thereby maintaining the position of the anvil assembly 260 with respect to the cartridge assembly 250 during actuation of end effector 230 (see FIG. 5). A release mechanism (not shown) could be provided to reverse rotate the pin 278 to reorient it for release through slot 292 to unapproximate the cartridge and anvil assemblies.

Figure 12:
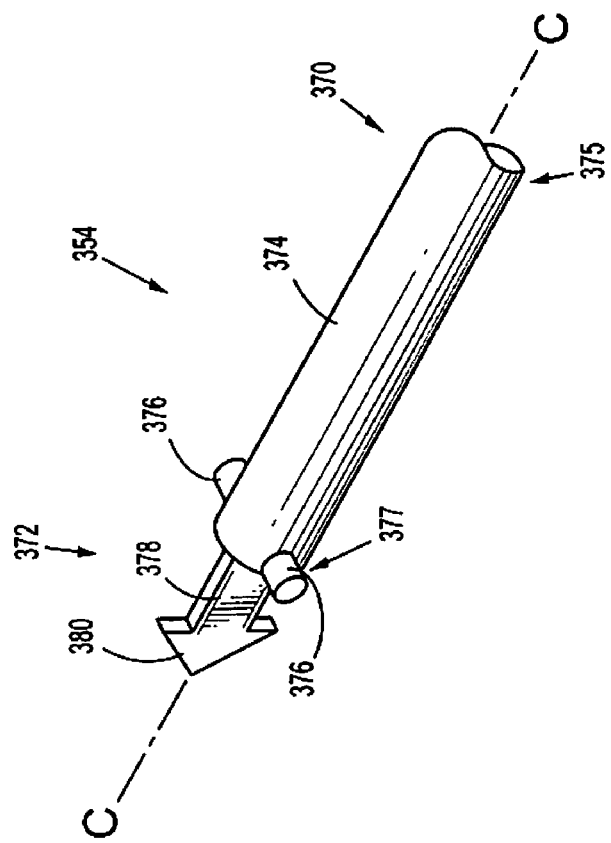
FIG. 12 is a perspective view of another embodiment of a pin for use with the end effector shown in FIG. 11.
Figure 11:
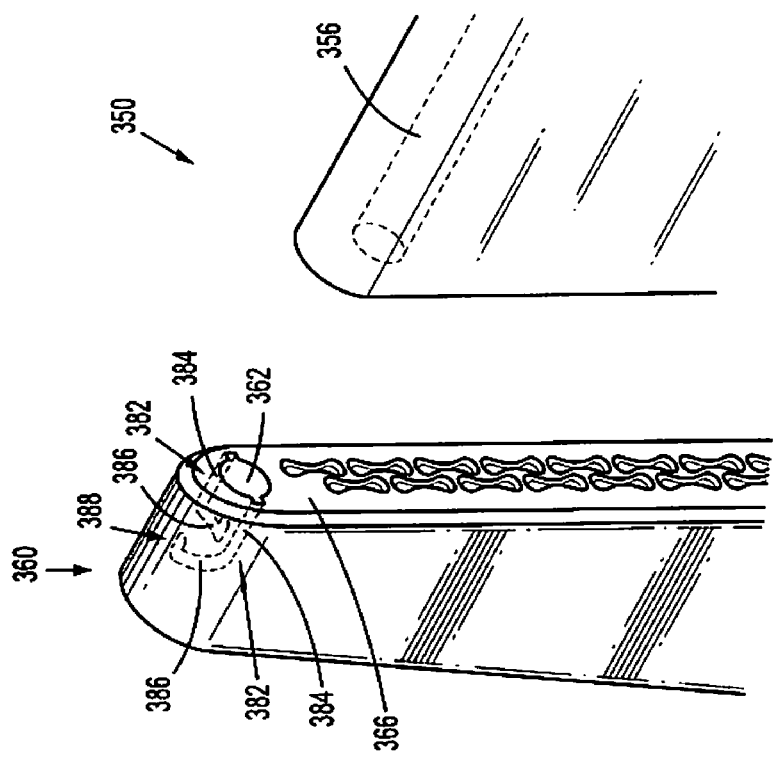
FIG. 11 is a perspective view of another embodiment of an end effector.

FIGS. 11 and 12 illustrate another embodiment of cartridge assembly 350 and anvil assembly 360 of a surgical stapling instrument such as instrument 100 of FIG. 1. In this embodiment, cartridge assembly 350 includes a bore 356 adapted to receive pin 354. Pin 354 includes a proximal portion 370 and a distal portion 372 and defines a longitudinal axis C-C therealong. A body 374 extends from proximal portion 370 of pin 354 to a location proximal to distal portion 372 of pin 354. Moreover, body 374 features a substantially cylindrical shape and has a proximal end 375 and a distal end 377. A pair of protrusions juts out radially from the distal end 377 of body 374. Pin 354 further includes an elongate plate 378 extending distally from distal end 377 of body 374. Elongate plate 378 has a substantially planar profile and extends between body 374 and engagement section 380. Distal portion 372 of pin 354 includes substantially flat engagement section 380 having a substantially triangular shape in the form of an arrowhead. As discussed in detail below, pin 354 is adapted to move longitudinally through bore 356 of cartridge assembly 350 and hole 362 of anvil assembly 350 in response to actuation of trigger 140 (see FIG. 1).

Anvil assembly 360 further includes at least one groove 382 formed along hole 362 for facilitating the reorientation of engagement section 380 during the firing process. In the embodiment shown in FIG. 11, anvil assembly 360 includes two grooves 382 arranged in diametrically opposed relation with respect to each other. Each groove 382 is configured to slidably receive a protrusion 376 and extends from a tissue-engaging surface 366 of anvil assembly 360 to an inner portion of anvil assembly 360. The geometry of each groove 382 allows pin 354 to slide initially longitudinally through bore 356 in a linear path and then rotate to change the orientation or position of engaging or head section 380 with respect to anvil assembly 360 and cartridge assembly 350. In some embodiments, each groove 382 includes a longitudinal or straight portion 384 and an arcuate or curved portion 386 located at a distal end 388 thereof which is directed slightly back in a proximal direction. The straight portion 384 of grooves 382 directs the initial longitudinal translation of pin 354 through hole 362, whereas the curved portion 386 guides the rotation of pin 254 about longitudinal axis C-C. The proximally extending portion helps define a lockout position so the pin needs to move distally first to disengage it from the grooves 382. This helps to prevent inadvertent rotation and backing out of the pin 354.

It should be appreciated that the other embodiments of pin receiving grooves disclosed herein could also be provided with a proximally directed groove portion as in FIG. 11 to require distal movement of the pin, followed by proximal movement, to disengage it from the groove in the anvil assembly.

As pin 354 moves distally as a result of the distal motion of pusher 122 (see FIGS. 3 and 4), protrusions 376 first slide along the straight portion 384 of grooves 382. Protrusions 376 eventually slide along the curved portion 386 of grooves 382 as a result of the continued distal advancement of pusher 122 and pin 354. When protrusions 376 move within the curved portion 386 of grooves 386, pin 354 rotates about longitudinal axis C-C. As pin 254 rotates about longitudinal axis C-C, engagement section 380 adjusts its position or orientation, thereby securing pin 354 to anvil assembly 360. If the proximally directed straight portion is provided at the end of the curve as described above, after rotation, the protrusions 354 will move slightly proximally as they move within this straight portion. As shown, the pin 384 rotates about 180 degrees, however it should be appreciated that other degree rotation for pin 384 as well as for the other pins disclosed herein are also contemplated to lock the pin with respect to the anvil assembly.

FIGS. 13-15 illustrate the operational stages of pin 354 during actuation of a surgical stapling instrument such as instrument 100 of FIG. 1. Pin 354 works along with a locking structure 390 disposed in anvil assembly 360 to minimize or prevent anvil assembly 360 from cantilevering away from cartridge assembly 350 during firing. Hole 362 of anvil assembly 360 leads to locking structure 390. The structure and operation of locking structure 390 is substantially similar to the structure and operation of locking structure 290 of FIGS. 9 and 10. Locking structure 390 includes a slot 392 positioned at a proximal end 394 thereof and a cavity 396 located at distal end 398 thereof. Cavity 396 is disposed in communication with slot 392. Slot 392 is configured to receive engagement section 380 and at least a portion of elongate plate 378 while pin 354 is oriented in a first position as shown in FIG. 14. Cavity 396 can receive engagement section 380 when pin 354 is oriented in either the first position (as seen in FIG. 14) or the second position (as depicted in FIG. 15). When engagement section 380 is positioned inside cavity 396, the geometry of cavity 396 and slot 392 precludes or at least inhibits engagement section 380 from exiting anvil assembly 360 if pin 354 is oriented in the second position as shown in FIG. 15. The secure engagement between engagement section 380 and cavity 396 maintains the position of anvil assembly 360 with respect to cartridge assembly 350 during actuation of end effector 130 (see FIG. 1), thereby impeding or hindering anvil assembly 360 from cantilevering away from cartridge assembly 350.

When a user actuates trigger 140 (see FIG. 1), pin 354 is moved distally and eventually reorients engagement section 380 from the first position toward the second position. While pin 354 moves distally, protrusions 376 initially slide along the straight portion 384 of grooves 382. At this moment, pin 354 translates longitudinally through hole 362. While pin 354 translates in a distal direction, engagement section 380 is oriented in the first position (as seen in FIGS. 13 and 14) and is therefore capable of passing through slot 392 of locking structure 390. The continued longitudinal motion of pin 354 through hole 362 drives protrusions 376 toward the curved portion 386 of grooves 382. The length of straight portion 384 allows protrusions 376 to reach the curved portion 386 of grooves 382 just as engagement section 380 enters cavity 396. At this point, pin 354 begins to rotate about longitudinal axis C-C, reorienting engagement section 380 from the first position (as shown in FIG. 14) to the second position (as illustrated in FIG. 15). Engagement portion 380 is already positioned inside cavity 396 when protrusions 376 slide along the curved portion 386 of groove 282. Once engagement portion 380 rotates to its second position, the geometry of cavity 396 blocks engagement portion 380 from exiting anvil assembly 360, (by the wall of cavity 396) thereby maintaining the position of the anvil assembly 360 with respect to the cartridge assembly 350 during actuation of end effector 130 (see FIG. 1).

FIGS. 16 and 17 show a cartridge assembly 450, an anvil assembly 450, and a pin 454 for use in conjunction with a surgical instrument such as instrument 100 of FIG. 1. Anvil assembly 460 is substantially identical to anvil assembly 260 (see FIG. 5). Cartridge assembly 450 includes a bore 456 adapted to slidably receive pin 454. Pin 454 includes a proximal portion 470 and a distal portion 472 and defines a longitudinal axis D-D therealong. The proximal portion 470 of pin 454 includes a substantially cylindrical body 474. Cylindrical body 474 has one or more grooves 476 formed thereon. Grooves 476 are arranged in a diametrically opposed relation with respect to each other and each is adapted to slidably receive a protrusion 482 disposed in cartridge 450 as discussed in detail below. In addition to grooves 476, pin 454 includes an elongate plate 478 extending from body 474 to an engagement section 480 positioned in distal portion 472. Elongate plate 478 has a substantially planar configuration. Engagement section 480 has a substantially triangular shape. During operation, engagement section 480 secures pin 454 to anvil assembly 460 after pin 454 has been advanced distally through bore 456 of cartridge assembly 450.

Cartridge assembly 450 incorporates one or more protrusions 482 extending inwardly toward bore 456. Each protrusion 482 has a straight portion 484 spanning alongside a partial length of bore 456 and an arcuate or curved portion 486 located at a distal end 488 thereof. The curl of curved portions 486 of each protrusion 482 follows the circumference of bore 456. Each protrusion 482 is adapted to be slidably received by a groove 476 of pin 456. The geometry of each protrusion 482 enables pin 454 to initially slide through bore 456 upon a distal advancement of pusher 122 (see e.g. FIGS. 3 and 4) and subsequently rotate about longitudinal axis D-D, reorienting engagement section 480 from a first position to a second position. When engagement portion 480 is oriented in the first position, elongate plate 478 and engagement portion 480 are able to enter inside a locking structure (not shown) of anvil assembly 460. The structure and operation of locking structure of anvil assembly 460 is substantially identical to locking structure 290 shown in FIGS. 9 and 10. Like locking structure 290, the locking structure of anvil assembly 460 traps engagement section 480 of pin 454 inside anvil assembly 460 after engagement section 480 has been distally moved into anvil assembly 460 and reoriented to the second position.

In operation, pin 454 moves distally toward anvil assembly 460 upon actuation of trigger 140 (see FIG. 1). Initially, pin 454 translates distally through bore 456. The sliding engagement between grooves 476 of pin 454 and the straight portion 484 of protrusions 482 guide the distal translation of pin 454. Due to the continued distal advancement of pin 454, grooves 476 of pin 454 eventually engage the curved portion 486 of protrusions 482. As grooves 476 slide along the curved portion 486 of protrusions 482, pin 454 rotates about longitudinal axis D-D and reorients engagement portion 480 from a first position to a second position. The geometry of protrusions 482 allows pin 454 to rotate about longitudinal axis D-D once engagement portion 480 is located within a cavity (not show) of the locking structure. At this point, pin 454 is secured to anvil assembly 460. A release can be provided as in the other embodiments herein to rotate the pin to reorient it for removal.

FIGS. 18-21 illustrate an alternate embodiment of a cartridge assembly 550, an anvil assembly 560, and a pin 554 for use with a surgical instrument such as instrument 100 of FIG. 1. Cartridge assembly 550 includes a bore for slidably receiving pin 554. Pin 554 has a proximal portion 570 and a distal portion 572 and defines longitudinal axis E-E therealong. Distal portion 572 of pin 554 incorporates an engagement section or hook 580. Hook 580 has a first securing surface 582 defining a substantially right angle relative to longitudinal axis E-E and a first camming surface 584 defining an oblique angle with respect to longitudinal axis E-E. In use, hook 580 secures pin 554 to anvil assembly 560 to maintain the position of anvil assembly 560 with respect to cartridge assembly 550 during firing of the surgical stapling instrument.

Anvil assembly 560 has a slot 562 configured to receive pin 554. Slot 562 extends from tissue-engaging surface 566 to an inner portion of anvil assembly 560. Further, slot 562 has a lower surface 590 defining a plane F. Lower surface 590 extends from tissue-engage surface 566 to locking structure or catch 594. Locking structure 594 includes a second camming surface 592 defining an oblique angle relative to plane F and a second securing surface 596 defining a substantially right angle with respect to plane F and formed distal of camming surface 592. Second camming surface 592 is configured to slidably engage first camming surface 584 of pin 554. In one embodiment, the oblique angle defined by second camming surface 592 is complementary to the oblique angle defined by first camming surface 584. In use, pin 554 securely engages locking structure 594 when first securing surface 582 of pin 554 abuts second securing surface 596 of locking structure 594.

As shown in FIGS. 19-21, hook 580 reaches locking structure 594 when pin 554 is moved distally by any suitable means. In one embodiment, an actuation of trigger 140 (see FIG. 1) prompts the distal translation of pin 554 as seen in FIG. 19. As pin 554 moves continuously in a distal direction, first camming surface 584 of hook 580 slides on second camming surface 592 of locking structure 594, causing pin 554 to move away from lower surface 590, as seen in FIG. 20. Due to the continued distal advancement of pin 554, first camming surface 584 ultimately passes second camming surface 592 to allow first securing surface 582 to engage second securing surface 596. Once first securing surface 582 contacts second securing surface 596, locking structure 594 secures pin 554 in anvil assembly 560, thereby maintaining the position of anvil assembly 560 relative to cartridge assembly 550. A mechanism can be provided to move the pin vertically over the second securing surface 596 to disengage the pin 554 from the surface 596 to allow retraction of the pin 554 and unapproximation of the cartridge and anvil assemblies.

FIGS. 22 and 23 show a pin 654, a cartridge assembly 650, and an anvil assembly 660 for use with a surgical stapling instrument such as instrument 100 of FIG. 1. Cartridge assembly 650 includes a bore 656 adapted to receive pin 654. Pin 654 has a proximal portion 670 and a distal portion 672 and defines a longitudinal axis G-G therealong. Proximal portion 670 of pin 654 includes a body 674 and two protrusions 676 extending radially from body 674. Although FIG. 23 shows body 674 with a substantially cylindrical shape, body 674 may have any suitable shape or configuration. An elongate member 678 extends between proximal and distal portions 670, 672. Distal portion 672 of pin 654 has an external thread 680 formed thereabout. External thread 680 is configured for threadedly engaging an inner thread 692 of anvil assembly 660. As a consequence, pin 654 secures cartridge assembly 650 to anvil assembly 660.

Cartridge assembly 650 includes a bore 656 for receiving pin 654, as discussed above, and a pair of grooves 682 each adapted to slidably receive a protrusion 676 of pin 654. Grooves 682 are disposed alongside bore 656 and include a straight portion 684 and spiral portion 686 located at a distal end 688 thereof. In the depicted embodiment, spiral portion 686 includes multiple loops. When pin 654 moves through bore 656 in a distal direction, the geometry of grooves 682 allows pin 654 to initially advance longitudinally and later translate longitudinally and rotate about longitudinal axis G-G. While pin 654 rotates about longitudinal axis G-G, external thread 680 threadedly engages a locking structure 690 of anvil assembly 660.

Anvil assembly 660 includes hole 662 extending from a tissue-engaging surface 666 to locking structure 690. Locking structure 690 is disposed within anvil assembly 660 and includes an inner thread 692 formed around hole 662. Inner thread 692 is adapted to securely engage external thread 680 of pin 654.

Figure 24:
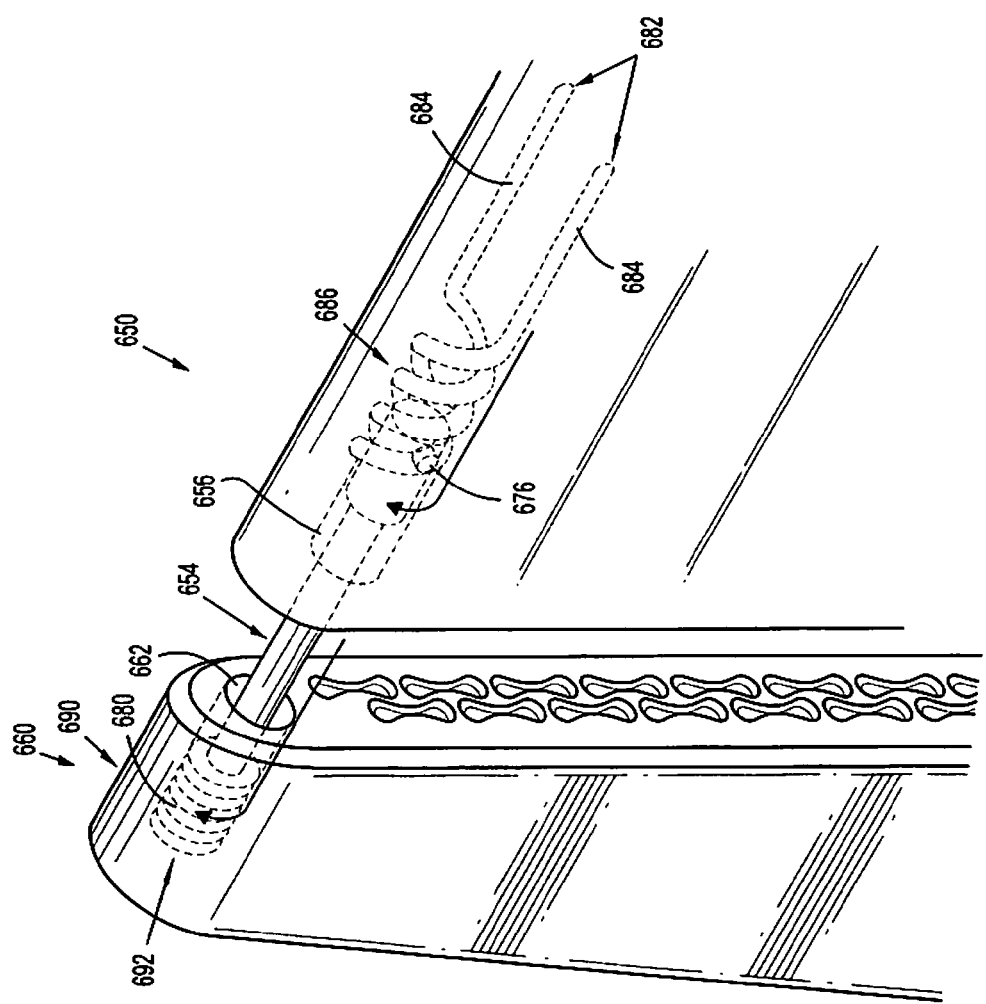
FIG. 24 is a perspective view of the end effector illustrated in FIG. 22 with the pin depicted in FIG. 23 positioned therein in the engaged position.

FIG. 24 illustrates the operation of pin 654. During operation, pin 654 fixes the position of anvil assembly 660 with respect to cartridge assembly 650, preventing or at least hindering anvil assembly 660 from cantilevering away from cartridge assembly 650 during firing of the surgical stapling instrument. Pin 654 moves distally in response to actuation of trigger 140 which approximates the cartridge and anvil assemblies as discussed above. During this distal motion of pin 654, grooves 682 (in conjunction with protrusions 676) guide the movement of pin 654 through bore 656. In particular, protrusions 676 first slide along the straight portion 684 of grooves 682 during the distal advancement of pin 654. While protrusions 676 slide along straight portions 684, pin 654 does not rotate and merely translates distally toward anvil assembly 660. Then, pin 654 moves into anvil assembly 660 through hole 662 and external thread 480 engages inner thread 692 when protrusions 676 slide along the spiral portion 686 of grooves 686. While protrusions 676 slide along the spiral portion 686 of grooves 686, pin 654 rotates about longitudinal axis G-G (see FIG. 23) and also moves distally toward anvil assembly 660, causing external thread 680 of pin 654 to threadedly engage inner thread 692 of locking structure 690 to secure pin 654 to anvil assembly 660. A mechanism for reverse rotation of pin 654 can be provided to retract the pin to unapproximate the cartridge and anvil assemblies.

With reference to FIGS. 25 and 26, a cartridge assembly 750, an anvil assembly 760, and pin 754 work similar to cartridge assembly 650, anvil assembly 660, and pin 654 in that there is threaded engagement. Pin 754, however, is manually secured to anvil assembly 760 and the cartridge does not have a spiral groove. As shown in FIG. 25, pin 754 has a proximal portion 770 and distal portion 772 and defines a longitudinal axis H-H. Proximal portion 770 of pin 754 includes a knob or handle 774 rotatable about longitudinal axis H-H. Knob 774 is adapted to be manually rotated. An elongate member 778 extends between knob 774 and distal portion 772. In operation, rotating knob 774 causes the rotation of elongate member 778 and distal portion 772. Distal portion 772 includes an external thread 780 formed thereabout. External thread 780 of pin 754 facilitates secure engagement between cartridge assembly 750 and anvil assembly 760.

Cartridge assembly 750 includes a bore adapted to receive pin 754. Knob 774 is positioned outside of cartridge assembly 750. The position of knob 774 relative to cartridge assembly 750 allows users to manipulate knob 774 manually. As pin 754 rotates about longitudinal axis H-H, external thread 780 threadedly engages a locking structure 790 of anvil assembly 760.

Anvil assembly 760 has a hole 762 and a locking structure 790 for securing pin 754 to anvil assembly 760. Locking structure 790 includes an inner thread 792 formed about hole 762. Inner thread 792 is configured to threadedly engage external thread 780 of pin 754.

In operation, a user actuates trigger 140 (such as in FIG. 1) to advance cartridge assembly 750 toward anvil assembly 760. After actuating trigger 140, the user rotates pin 754 through knob 774 to thread pin 754 into hole 762. As the user rotates knob 774, external thread 780 rotates about longitudinal axis H-H and securely engages inner thread 792 of locking structure 790, thereby securing pin 754 to anvil assembly 760. Reverse rotation of knob 774 unthreads pin 754 from thread 792 to withdraw the pin 754 for unapproximation of the cartridge and anvil assemblies.

Figure 28:
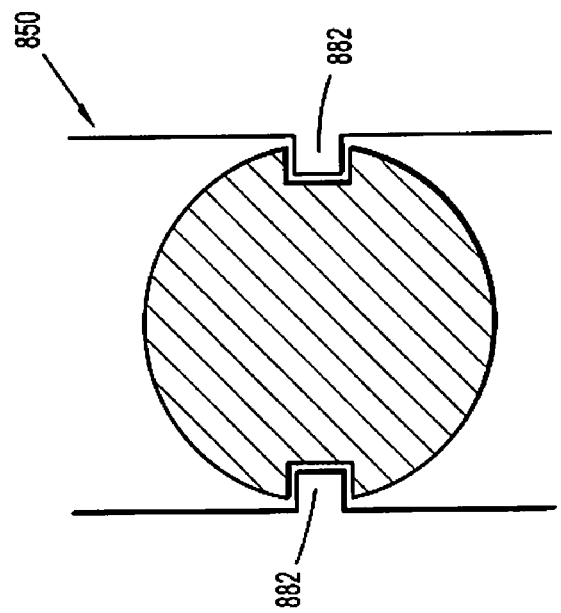
FIG. 28 is a front cross-sectional view of the pin illustrated in FIG. 27 positioned in an end effector.
Figure 27:
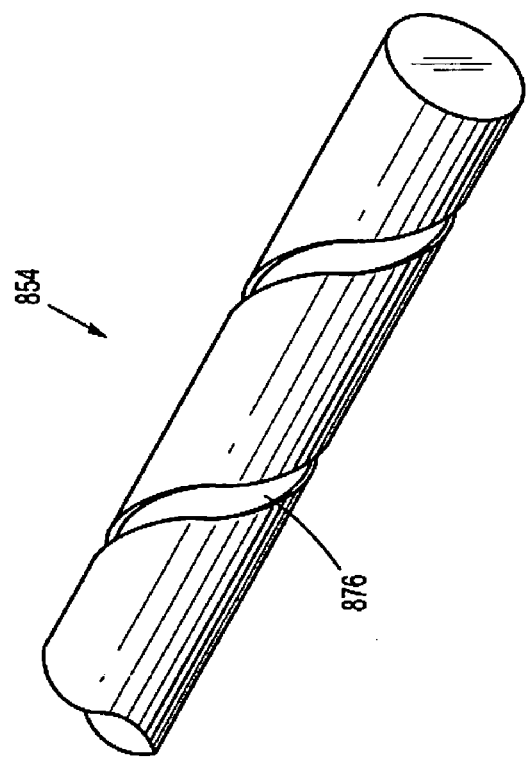
FIG. 27 is a perspective view of another alternate embodiment of a pin.

FIGS. 27 and 28 depict an alternative embodiment of pin 854 and cartridge assembly 850. The structure and operation of pin 854 and cartridge assembly 850 is substantially similar to the structure and operation of pin 654 and cartridge assembly 650 of FIG. 23. In this embodiment, cartridge assembly 850 has protrusions 882 instead of grooves 682 and pin 854 includes grooves 876 in lieu of protrusions 676. Protrusions 882 extend longitudinally along cartridge assembly 850, whereas grooves 876 swirl around pin 854 in a helical fashion.

The sliding engagement between grooves 876 and protrusions 882 guide the movement of pin 854 through cartridge assembly 850. In use, as pin 854 is pushed distally, grooves 876 cause pin 854 to rotate while moving in a distal direction. Pin 854 may include an external thread at a distal end thereof for engaging an anvil assembly (not shown), thereby forming a locking structure in a similar manner as the external thread 680 of pin 654 and the inner thread 690 of anvil assembly 660 of FIGS. 22 and 23.

FIGS. 29-32 show another embodiment of cartridge assembly 950, anvil assembly 960, and pin 954. Cartridge assembly 950 includes a bore (not shown) adapted to receive pin 954. Anvil assembly 960 includes a locking structure 990 for securing pin 954 inside anvil assembly 960. Pin 954 has a proximal portion 970 and a distal portion 972 and defines a longitudinal axis I-I. Distal portion 972 of pin 954 includes an engagement section or hook 980. Hook 980 has a first securing surface 982 defining a substantially right angle relative to longitudinal axis I-I and a first camming surface 984 defining an oblique angle with respect to longitudinal axis I-I. In use, hook 980 fixes pin 954 to anvil assembly 960 to maintain the position of anvil assembly 960 with respect to cartridge assembly 950 during firing of a surgical stapling instrument such as instrument 100 of FIG. 1.

Anvil assembly 960 has a slot 962 adapted to receive pin 954. Slot 962 leads to a locking structure 990 disposed in anvil assembly 960. Locking structure 990 includes a hook or catch 992 pivotally coupled to anvil assembly 960 and a biasing member 994 configured to bias catch 992. In one embodiment, a pivot pin 996 pivotally connects catch 992 to anvil assembly 992. Catch 992 has a second camming surface 998 adapted to slidably engage first camming surface 984 and a second securing surface 999 configured to abut first securing surface 982.

In use, locking structure 990 fixes the position of anvil assembly 960 with respect to cartridge assembly 950 through pin 954. First, when a user actuates trigger 140 (such as in FIG. 1) to approximate the cartridge and anvil assemblies and move pin 954 in a distal direction, pin 954 enters anvil assembly 960 through slot 962 and engages locking structure 990. Specifically, first camming surface 984 slides on second camming surface 998, displacing catch 992 away from pin 954 against the influence of biasing member 994 as seen in FIGS. 30 and 31. After first camming surface 984 slides distally beyond second camming surface 998, biasing member 994 biases catch 992 toward pin 954 and, as a result, first securing surface 982 fixedly engages second securing surface 999, thereby locking pin 954 to anvil assembly 960. That is, abutment of the securing surface 982 with the securing surface 999 prevents proximal movement of pin 954. A release mechanism can be provided to separate the surfaces 982 and 999 (e.g. by lifting hook 980 upwardly or forcing catch 992 downwardly as viewed in the orientation of FIG. 32) to allow the pin 954 to pass proximally over the securing surface 999 to enable retraction (unapproximation) of the cartridge and anvil assemblies.

FIG. 33 shows an alternate embodiment of pin 1054 attached to a cartridge assembly (not shown) and an anvil assembly (not shown) with a locking structure 1090. Pin 1054 has a proximal portion (not shown) and a distal portion 1072. An elongate body 1086 extends between the proximal portion and distal portion 1072. Distal portion 1072 of pin 1054 includes an engagement section 1080 configured to be attached to locking structure 1090. Engagement section 1080 incorporates an annular recess 1082 formed thereabout and tip 1084 having a tapered configuration. In an alternate embodiment, tip 1084 has rounded shape as seen in FIG. 37. Tip 1084 is adapted to securely engage locking structure 1090.

Locking structure 1090 includes one or more pieces of sheet metal 1092 fixed to the anvil assembly (not shown). Alternatively, sheet metal 1092 is an integral part of the anvil assembly. Sheet metal 1092 has a hole 1094 with a diameter smaller than the diameter of pin 1054. Hole 1094 can contract and expand when sheet metal 1092 deforms. Sheet metal 1092 deforms when subject to stress and it returns to its original configuration when the stress is removed or decreased. In one embodiment, sheet metal 1092 is made of a shape memory material capable of transitioning between an original configuration and a stressed configuration upon imposition or removal of stress. Other materials are also contemplated.

With reference to FIGS. 34-35, pin 1054 secures anvil assembly (not shown) to cartridge assembly (not shown) during actuation of a surgical stapling instrument such as instrument 100 of FIG. 1. In operation, a user fires surgical stapling instrument 100 by actuating trigger 140 (see FIG. 1). In response to such actuation, the cartridge and anvil assemblies are approximated and pin 1054 advances distally toward locking structure 1090. As with the other embodiments of the pins disclosed herein, in alternate embodiments the user can optionally move pin 1054 manually. Pin 1054 moves distally toward sheet metal 1092 and then tip 1084 forces its way into hole 1094. As tip 1084 passes through hole 1094, sheet metal 1092 deforms and consequently expands hole 1094 to allow the passage of tip 1084. After tip 1084 passes through hole 1094, hole 1094 contracts around annular recess 1082, thereby locking pin 1054 to sheet metal 1092, as the diameter of the pin adjacent the recess 1082 exceeds the diameter of the hole 1094.

Figure 40:
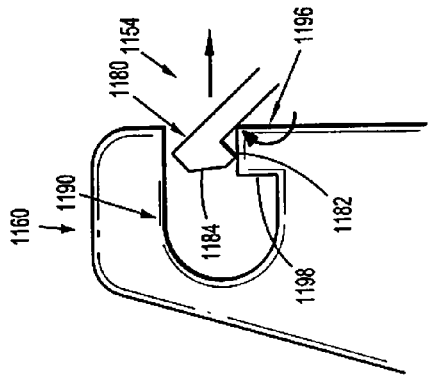
FIGS. 38-40 are side views of another alternate embodiment of a pin and an end effector at different stages of operation.
Figure 39:
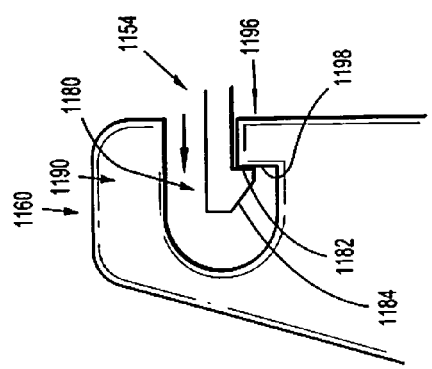
Figure 38:
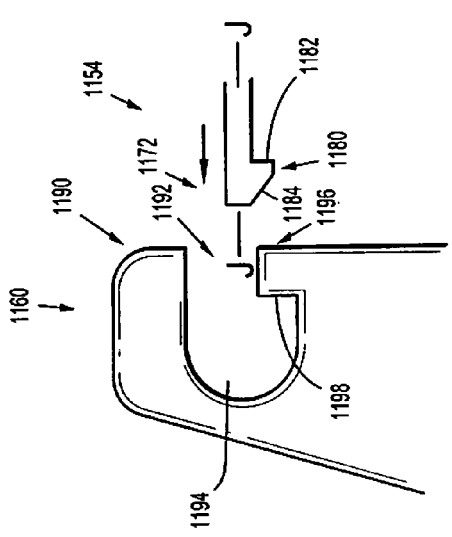

FIGS. 38-40 show an alternate embodiment of a pin 1154 and an anvil assembly 1160 with a locking structure 1190. Pin 1154 is configured to pivot and has a proximal portion (not shown) and a distal portion 1172. Moreover, pin 1154 defines a longitudinal axis J-J therealong. Distal portion 1172 of pin 1154 includes a hook or engagement section 1180 adapted to interact with locking structure 1190. Engagement section 1180 includes a first securing surface 1182 defining a substantially right angle relative to longitudinal axis J-J and a first camming surface 1184 oblique with respect to longitudinal axis J-J. In use, engagement section 1180 secures pin 1154 to anvil assembly 1160 to maintain the position of anvil assembly 1160 with respect to a cartridge assembly (not shown) during actuation of a surgical stapling instrument such as instrument 100 of FIG. 1.

Locking structure 1190 of anvil assembly 1160 includes an aperture 1192 leading to a cavity 1194 located inside of anvil assembly 1160. Aperture 1192 is configured to receive pin 1154. Locking structure 1190 further includes a wall 1196 extending upwardly as viewed in the orientation of FIG. 38. Wall 1196 has a second securing surface 1198 adapted to engage first securing surface 1182 of pin 1154. The wall can be integral or can be a separate component attached to the anvil assembly.

During operation, a user moves pin 1154 distally (manually or mechanically through trigger 140) to insert engagement section 1180 inside cavity 1194. As pin 1154 translates distally, engagement section 1180 first passes through aperture 1192 until it reaches cavity 1194. Note the contact of wall 1198 cams the camming surface upwardly to ride over the wall and then downwardly into the position of FIG. 39. Once engagement section 1180 of pin 1154 is positioned within cavity 1194, first securing surface 1182 contacts second securing surface 1198 of wall 1196, thereby locking pin 1154 to anvil assembly 1160 as the abutting surfaces 1192 and 1198 prevent proximal movement of pin 1154. To release pin 1154 from anvil assembly 1160 for unapproximation of the cartridge and anvil assemblies, the user pivots pin 1154 upwardly away from wall 1196 as shown in FIG. 40 by a release mechanism (not shown) operatively connected to pin 1154. After pin 1154 has been pivoted away from wall 1196 to disengage surface 1198, the user can move pin 1154 proximally toward its original position.

Figure 42:
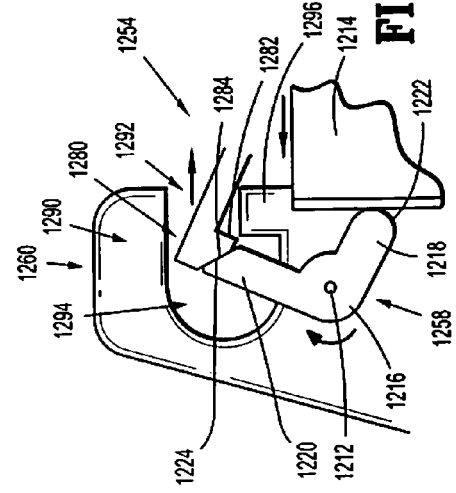
FIGS. 41 and 42 are side views of an alternate embodiment of a pin and an end effector at different stages of operation.
Figure 41:
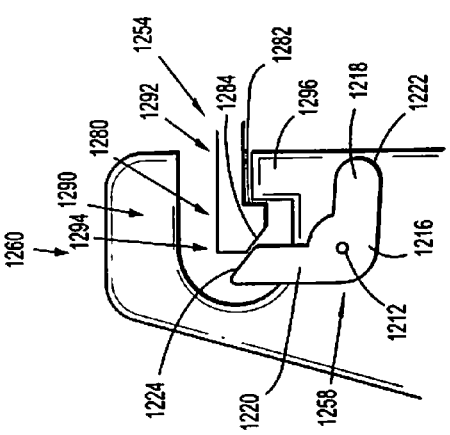

FIGS. 41 and 42 show an alternative embodiment of an anvil assembly 1260 with a locking structure 1260 and a pin 1254. Pin 1254 is substantially similar to pin 1154. Like pin 1154, pin 1254 has an engagement section 1280 and is configured to pivot toward and away from locking structure 1290. Locking structure 1290 is substantially similar to locking structure 1190. As in locking structure 1190, locking structure 1290 includes an aperture 1292, a cavity 1294, and wall 1296. In addition to aperture 1292, cavity 1294, and wall 1296, locking structure 1290 features a cam lever 1258 rotatably connected to anvil assembly 1260. Cam lever 1258 includes a central portion 1216, and first and second legs 1218, 1220 extending from central portion 1216. A pin 1212, or any other suitable member(s), rotatably couples central portion 1216 of cam lever 1258 to anvil assembly 1260. Cam lever 1258 is adapted to rotate about pin 1212 between a first position, as seen in FIG. 41, and a second position, as depicted in FIG. 42, upon engagement or disengagement with a knife 1214. In this embodiment, the surgical stapling instrument such as instrument 100 of FIG. 1 includes knife 1214 or any other suitable cutting device capable of advancing distally.

During operation, advancement of knife 1214 by a trigger, e.g. trigger 140 of FIG. 1, pushes first leg 1218 to effect the rotation of cam lever 1258 about pin 1212. First leg 1218 of cam lever 1258 has an abutting surface 1222 adapted to engage knife 1214, and second leg 1220 has a camming surface 1224 adapted to engage the camming surface 1284 of engagement section (or hook) 1280.

In operation, actuating 140 (FIG. 1) advances pin 1254 distally to insert pin 1254 inside cavity 1294. In some embodiments, the user can translate pin 1254 manually. During translation, pin 1254 passes through aperture 1292 into cavity 1294, cammed upwardly as described above with pin 1154 of FIG. 38, and then securing surface 1282 of pin 1254 engages wall 1296, locking pin 1254 to anvil assembly 1260 due to the abutment of securing surface 1282 and the inner surface of wall 1296. At this moment, cam lever 1258 is oriented in the first position as shown in FIG. 41. After pin 1254 has been fixed to anvil assembly 1260, the user actuates the firing mechanism to advance fasteners from the approximated cartridge assembly. Such actuation advances knife 1214 in a distal direction to rotate cam lever 1258. Specifically, knife 1214 pushes abutting surface 1222 of first leg 1218. As a result, cam lever 1258 rotates about pin 1212 to the second position, as shown in FIG. 42. While cam lever 1258 rotates toward the second position, camming surface 1224 of second leg 1220 engages camming surface 1284 of engagement section 1280, thereby causing pin 1254 to pivot in the direction of the arrow to release engagement section 1280 from locking structure 1290 as surface 1282 is forced out of engagement with wall 1296. It should be appreciated that other mechanisms can be used to rotate clam lever 1258 to pivot pin 1254. For example, a tab or other engaging structure can extend from the knife bar, or be actuated by the knife bar, to pivot cam lever 1258. Tabs or structures operable independent of the knife could also be provided.

Figure 43:
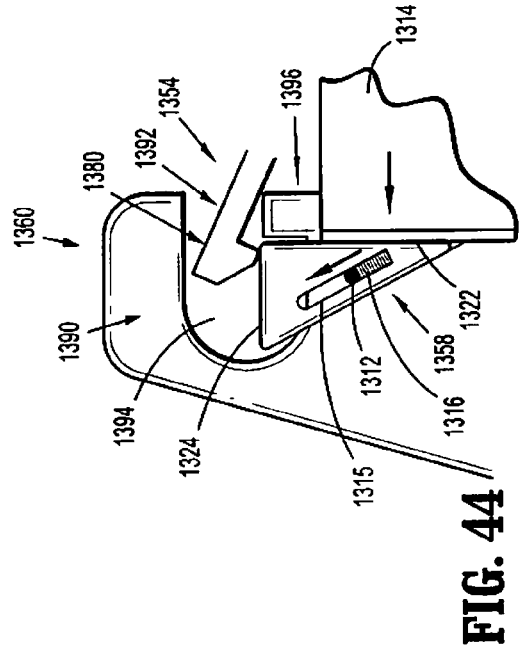
FIGS. 43 and 44 are side views of another alternate embodiment of a pin and an end effector at different stages of operation.
Figure 44:
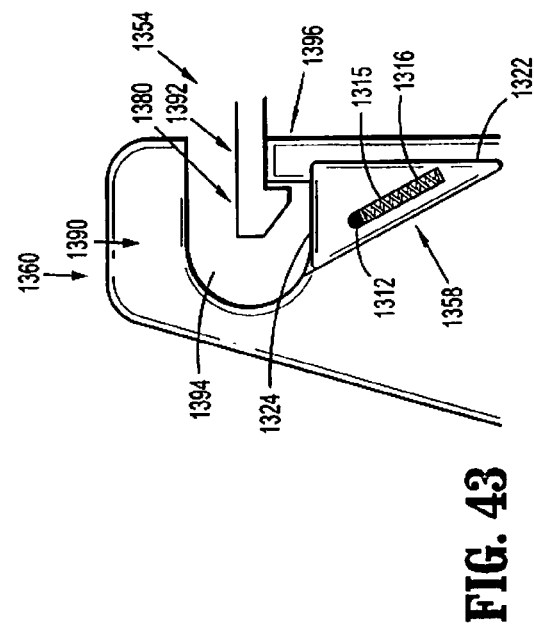

FIGS. 43 and 44 illustrate another embodiment of a pin 1354 and an anvil assembly 1360 with a locking structure 1390. Pin 1354 is substantially similar to pin 1154 as pin 1354 contains an engagement section or hook 1380 and is configured to pivot away and toward locking structure 1390. Locking structure 1390 is substantially similar to locking structure 1160 as locking structure 1390 includes an aperture 1392, a cavity 1394, and wall 1396. Locking structure 1390 also includes a camming member 1358 adapted to push engagement section 1380 of pin 1354. Camming member 1358 features a triangular shape and includes an abutting surface 1322 facing a knife 1314 and a camming surface 1324 facing pin 1354 when pin 1354 is positioned in cavity 1394. Moreover, camming member 1358 contains a diagonal slot 1315 configured for slidably receiving a sliding pin 1312. Sliding pin 1312 slidably couples camming member 1358 to anvil assembly 1360. In use, camming member 1358 slides with respect to anvil assembly 1360 between a first position, as seen in FIG. 43, and a second position, as shown in FIG. 44. Locking structure 1390 further includes a biasing member 1316, such as a spring, for biasing camming member 1358 away from cavity 1394. In this embodiment, the surgical stapling instrument such as instrument 100 of FIG. 1 includes knife 1314 configured to translate toward and away from anvil assembly 1360.

In operation, a user moves pin 1354 into cavity 1394 through aperture 1392, either automatically as the cartridge and anvil assemblies are approximated and/or in some embodiments manually. Once pin 1354 is positioned inside cavity 1394 (after the camming surface rides over the wall 1396), engagement section 1380 of pin 1354 engages wall 1396, thereby locking pin 1354 to anvil assembly 1360 as the abutment of the camming surface of the pin and the wall prevents proximal movement of the pin. The pin 1354 is released from anvil assembly 1360 by advancement of knife 1314 distally. As knife 1314 translates toward anvil assembly 1360, knife 1314 contacts abutting surface 1322 of camming member 1358 and pushes camming member 1358 toward cavity 1394, moving camming member 1358 from the first position toward the second position. While camming member 1358 moves from the first position to the second position, slot 1315 and sliding pin 1312 guide the motion of camming member 1358. During this motion, camming member 1358 pushes pin 1354 away from wall 1396 as shown in FIG. 44. As a consequence, engagement section 1380 of pin 1354 releases from wall 1396 of locking structure 1390, unlocking pin 1354 from anvil assembly 1360 to enable retraction of the pin 1354 and unapproximation of the cartridge and anvil assemblies. It should be appreciated that other mechanisms, e.g. a manual tab, could be utilized to move the camming member 1358 to move and release the pin 1354.

Figure 45:
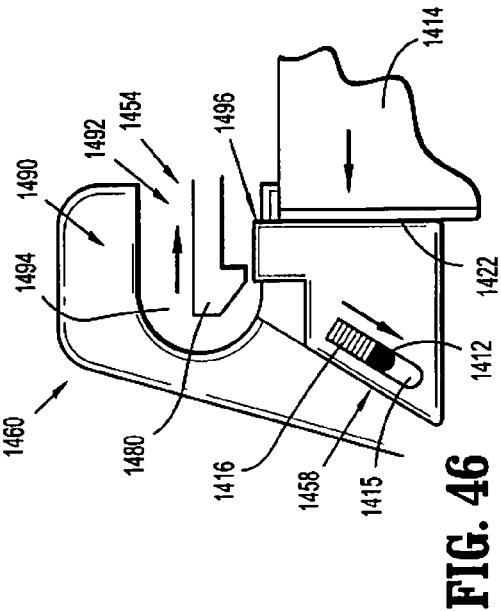
FIGS. 45 and 46 are side views of yet another alternate embodiment of a pin and an end effector at different stages of operation.
Figure 46:
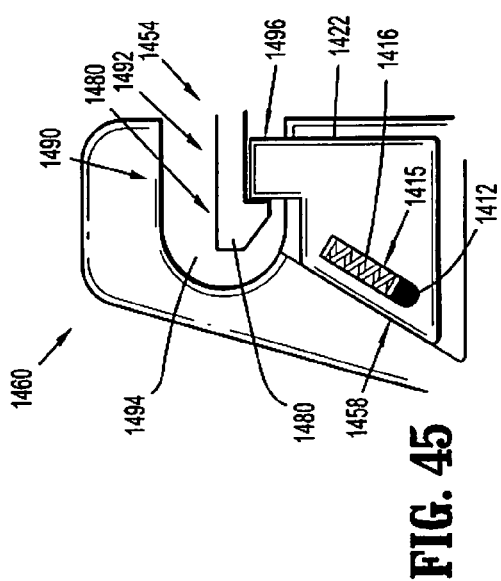

FIGS. 45 and 46 show an alternate embodiment of a pin 1454 and an anvil assembly 1460 with a locking structure 1490. Pin 1454 is substantially similar to pin 1154. Pin 1454 includes an engagement section or hook 1480 and is adapted to move longitudinally toward and away from anvil assembly 1460. Locking structure 1490 is substantially similar to locking structure 1190. Locking structure 1490 includes a cavity 1494, an aperture 1492 leading to cavity 1494, and a camming member 1458 configured to retain and displace pin 1454 from anvil assembly 1460. Camming member 1458 includes an abutting surface 1422 facing knife 1414, a wall 1496 extending toward cavity 1494, and a diagonal slot 1415 configured to slidably receive a sliding pin 1412. Sliding pin 1412 slidably connects camming member 1458 to anvil assembly 1460. During operation, camming member 1458 slides with respect to anvil assembly 1460 between a first position, as seen in FIG. 45, and a second position, as depicted in FIG. 46. In the first position, wall 1496 of camming member 1458 is partially located inside cavity 1494. In the second position, wall 1496 is located outside of cavity 1494, or at least sufficiently spaced from engagement section 1480 to allow proximal movement of pin 1480. Locking structure 1490 also includes a biasing member 1416, such as a spring, for biasing camming member 1458 toward cavity 1494. As shown in FIG. 46, a surgical stapling instrument such as instrument 100 of FIG. 1 includes a knife 1414 adapted to move longitudinally toward and away from anvil assembly 1460.

During use, a user moves pin 1454 distally into cavity 1494 through aperture 1492 either automatically as the cartridge and anvil assemblies are approximated and/or in some embodiments manually. The pin 1454 rides over the member 1458 and moves to the first position as seen in FIG. 45. When pin 1454 is located inside cavity 1494 and camming member 1458 is in the first position, engagement section 1480 engages wall 1496 of camming member 1458, locking pin 1454 to anvil assembly 1460 as the abutting surfaces prevent proximal movement of pin 1454. Biasing member 1416 maintains camming member 1458 in the first position. Advancement of knife 1414 distally toward anvil assembly 1460 releases pin 1454 from anvil assembly 1460 as the knife 414 pushes camming member 1458 in a distal direction moving camming member 1458 (along with wall 1496) away from cavity 1494. When wall 1496 moves away from cavity 1494, wall 1496 disengages from engagement section 1480 of pin 1454 (FIG. 46), releasing pin 1454 from anvil assembly 1460 for subsequent retraction. It should be appreciated that other mechanisms, e.g. a manual tab, could be utilized to move the camming member 1458 to release the pin.

Figure 48:
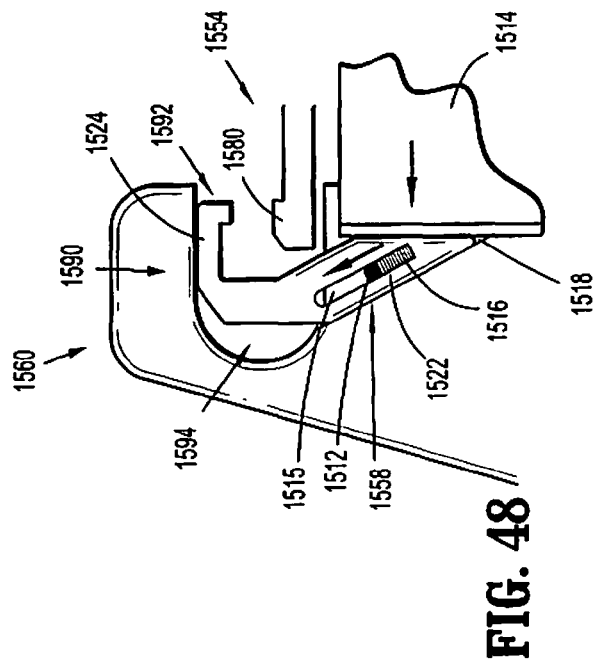
FIGS. 47 and 48 are side views of another alternate embodiment of a pin and an end effector at different stages of operation.
Figure 47:
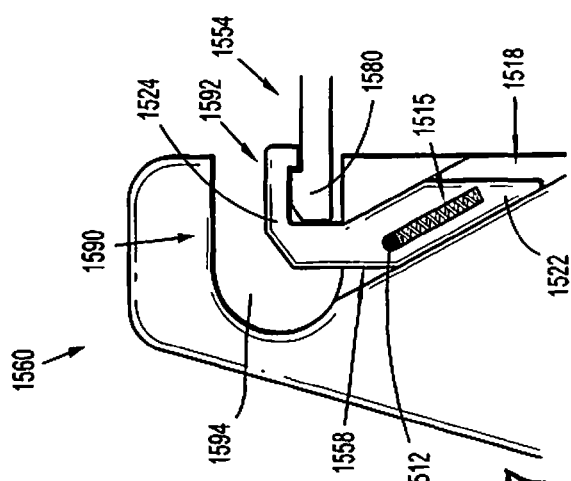

FIGS. 47 and 48 show an alternate embodiment of a pin 1554 and an anvil assembly 1560 with a locking structure 1590. Pin 1554 is substantially similar to pin 1154. Pin 1554 includes an engagement section 1580 and is configured to move longitudinally toward and away from anvil assembly 1560. Locking structure 1590 includes a cavity 1594, an aperture 1592 leading to cavity 1594, a camming member 1558 adapted to hold and release pin 1554, and a diagonal opening 1518 configured for slidably receiving at least a portion of camming member 1558. Camming member 1558 includes a slidable portion 1522 adapted to slide through diagonal opening 1518 and a clasp 1524 configured to hold engagement section 1580 of pin 1554. Portion 1522 of camming member 1558 includes a diagonal slot 1515 configured for receiving a sliding pin 1512. Sliding pin 1512 is fixed in anvil assembly 1560 and, along with diagonal slot 1515, guides the motion of camming member 1558 through anvil assembly 1560. A biasing member 1516, such as a spring, is disposed within diagonal slot 1515, and is adapted to bias camming member 1558 downwardly.

In this embodiment, a surgical stapling instrument such as instrument 100 of FIG. 1 includes a knife 1514 movable longitudinally away and toward anvil assembly 1560. When knife 1514 is advanced distally by a firing mechanism of the surgical stapling instrument, knife 1514 pushes slidable portion 1522 and exerts a distal force on camming member 1558. In response to such distal force, camming member 1558 moves from a first position (FIG. 47) toward a second position (FIG. 48). In the first position, clasp 1524 of camming member 1558 engages engagement section 1580 of pin 1554 and maintains pin 1554 secured to anvil assembly 1560. In the second position, clasp 1524 of camming member 1558 is spaced apart from engagement section 1580 when pin 1554 is located inside cavity 1594 and therefore does not hold pin 1554.

In operation, when pin 1554 is moved distally into cavity 1594 automatically upon approximation of the cartridge and anvil assemblies and/or in some embodiments manually, it forces the camming member 1558 slightly upwardly against the downward bias to slide under the engaging hook portion of clasp 1524. Once under the hook portion, the camming member 1558 returns to the first position to secure pin 1558 to anvil assembly 1560 due to the abutment of the surfaces. When camming member 1558 is located in the first position, clasp 1524 partially surrounds engagement section 1580 and secures pin 1554 to anvil assembly 1560 as shown in FIG. 47 by preventing proximal movement of pin 1554. Thereafter, when knife 1515 is advanced distally toward camming member 1558 by the firing mechanism, knife 1514 engages sliding portion 1522 of camming member 1558, urging camming member 1558 upwardly (in the orientation of FIG. 48) toward the second position. When camming member 1558 is in the second position, clasp 1524 is moved away from engagement section 1580, thereby releasing pin 1554 from anvil assembly 1560 as seen in FIG. 48 to allow retraction.

Figure 50:
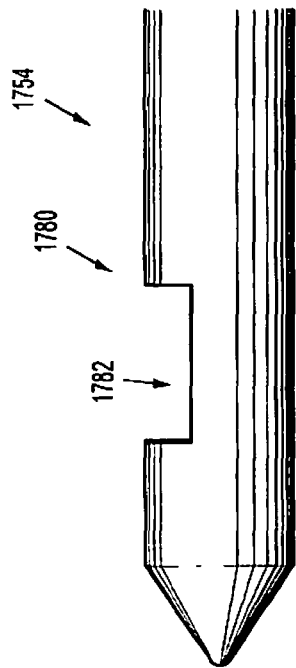
FIG. 50 is a side view of an alternate embodiment of a pin with a notch formed thereon.
Figure 49:
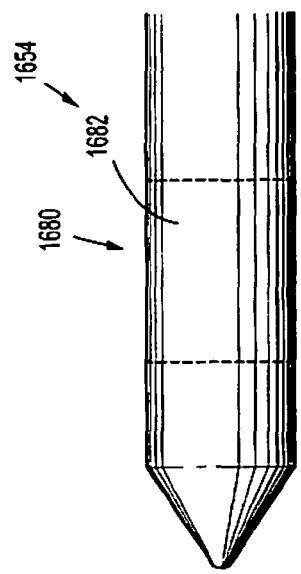
FIG. 49 is a side view of an embodiment of a pin with a slot formed therein.

FIGS. 49 and 50 illustrate alternate embodiments of pins for use with the disclosed embodiments. In FIG. 49, pin 1654 includes an engagement section 1680 with a transverse slot 1682. In FIG. 50, pin 1754 includes an engagement section 1780 with a notch 1782.

With reference to FIGS. 51 and 52, a pin 1854 and a locking structure 1890 for use with a surgical stapling instrument such as instrument 100 of FIG. 1 are disclosed. Pin 1854 defines a longitudinal axis K-K and has a proximal portion 1870 and a distal portion 1872. A cylindrical body 1874 extends from proximal portion 1870 to distal portion 1872. Distal portion 1872 incorporates an engagement section 1880 having a tapered configuration. The tapered configuration of engagement section 1880 extends from a proximal end 1882 of section 1880 to a distal tip 1884. The diameter of proximal end 1882 is larger than the diameter of cylindrical body 1874. Pin 1854 is disposed in a cartridge assembly (not shown) and is configured to move longitudinally toward and away from an anvil assembly (not shown).

Locking structure 1890 is positioned within the anvil assembly (not shown) and includes a latch 1892 pivotally connected to the anvil assembly. A pivot pin 1894, or any other suitable apparatus or means, pivotally couples latch 1892 to the anvil assembly. Latch 1892 is adapted to pivot transversely relative to longitudinal axis K-K between a first position (as seen in FIG. 51) and a second position (as shown in FIG. 52). In the first position, latch 1892 is separated from pin 1854 and therefore pin 1854 is free to move away from the anvil assembly. In the second position, latch 1892 engages pin 1854 and secures pin 1854 to anvil assembly. When latch 1892 is located in the second position, at least a portion of latch 1892 abuts proximal end 1882 of engagement section 1860, thereby fixing pin 1854 within the anvil assembly.

In use, a user first moves pin 1854 inside the anvil assembly, automatically upon approximation of the cartridge and anvil assemblies and/or in some embodiments manually, while latch is located in the first position as illustrated in FIG. 51. Then, the user pivots latch 1892 toward the second position as depicted in FIG. 52. When latch 1892 is located in the second position, latch 1892 engages engagement section 1860 of pin 1854, securing pin 1854 to the anvil assembly.

FIGS. 53 and 54 depict an alternate embodiment of a pin 1954 and a locking structure 1990 for use with surgical stapling instrument such as instrument 100 of FIG. 1. Pin 1954 is configured to move longitudinally from a cartridge assembly (not shown) between a proximal position and a distal position. Further, pin 1954 has a proximal portion (not shown) and a distal portion 1972. Distal portion 1972 of pin 1954 includes an engagement section 1980 adapted to be securely received by locking structure 1990. Engagement section 1980 has a tapered configuration forming an arrowhead like configuration and is adapted to be retained by locking structure 1990.

Locking structure 1990 is disposed in an anvil assembly (not shown) and includes a first jaw member 1992 and a second jaw member 1994. First and second jaw members 1992, 1994 are operatively connected to each other. A pivot pin 1996, or any other suitable member(s), pivotally interconnects first jaw member 1992 and second jaw member 1994. First and second jaw members 1992, 1994 are adapted to pivot between a first position, as seen in FIG. 53, and a second position, as depicted in FIG. 54. First and second jaw members 1992, 1994 are closer to each other in the first position than in the second position. Each of the first and second jaw members 1192, 1994 includes protrusions 1998 extending transversely therefrom. Locking structure 1990 further includes a biasing member 1982, such as a torsion spring, for biasing first and second jaw members 1992, 1994 toward their first position.

With reference to FIGS. 55-57, a user can employ locking structure 1990 to secure pin 1954 to the anvil assembly. Upon advancement of pin 1954 distally toward locking structure 1990 either automatically upon approximation of the cartridge and anvil assemblies and/or in some embodiments manually, pin 1954 subsequently forces its way into locking structure 1990. As pin 1954 advances into locking structure 1990, engagement section 1980 spreads apart first and second jaw members 1992, 1994, urging first and second jaw members 1992, 1994 toward the second position as seen in FIG.

55. Once engagement section 1980 is positioned within locking structure 1990, biasing member 1996 urges first and second jaw members 1992, 1994 to their first position, as seen in FIG. 56, thereby securing pin 1954 to the anvil assembly. Release of pin 1954 from the anvil assembly occurs as knife 1914 of a surgical stapling instrument such as instrument 100 of FIG. 1 advances in a distal direction, causing knife 1914 to engage protrusions 1998 and push first and second jaw members 1992, 1994 to their second position as seen in FIG. 57. After spreading apart first and second jaw members 1992, 1994 with knife 1914, pin 1954 can be moved proximally to disengage engagement section 1980 from locking structure 1990.

Figure 59:
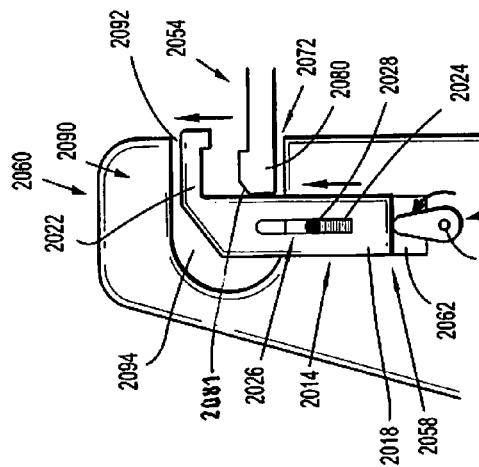
FIGS. 58 and 59 are side views of an alternate embodiment of a pin and an end effector including a cam mechanism for securing the pin, showing the cam mechanism at different stages of operation.
Figure 58:
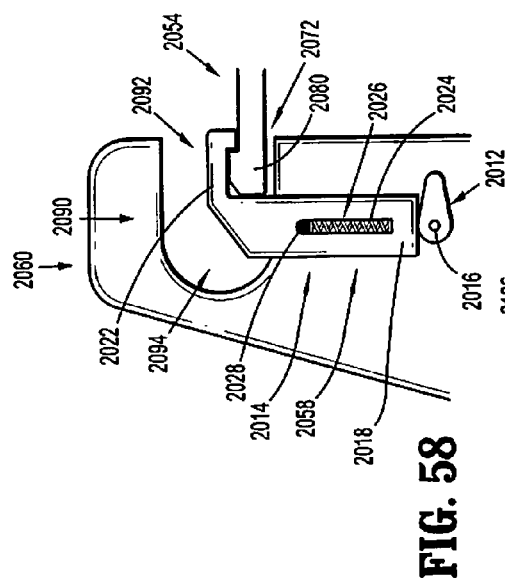

FIGS. 58 and 59 show an alternate embodiment of a pin 2054 and an anvil assembly 2060 with a locking structure 2090. Pin 2054 is substantially similar to pin 1554 of the embodiment of FIG. 28. Particularly, pin 2054 includes an engagement section 2080 disposed at a distal portion 2072 thereof. Engagement section 2080 is adapted to securely engage locking structure 2090.

Locking structure 2090 includes a cavity 2094, an aperture 2092 leading to cavity 2094, and camming mechanism 2058 adapted to hold and release pin 2054. Camming mechanism 2058 includes a cam 2012 rotatably connected to anvil assembly 2060 and a clasp 2014 slidably disposed in a longitudinal opening 2062 of anvil assembly 2060. A pivot pin 2016, or any other suitable member(s), pivotally connects cam 2012 to anvil assembly 2060. Clasp 2014 contains a cam follower 2018 at least partially disposed in longitudinal opening 2062 and a clasping section 2022 adapted to surround and hold engagement section 2080 of pin 2054. Cam follower 2018 is operatively associated with cam 2016 such that cam follower 2018 moves longitudinally in response to a rotation of cam 2016. Since cam follower 2018 is connected to (or alternatively integral with) clasping section 2022, the longitudinal motion of cam follower 2018 causes clasping section 2022 to move axially from a first position, as depicted in FIG. 58, to a second position, as shown in FIG. 59. In the first position, clasping section 2022 engages and partially surrounds engagement section 2080 of pin 2054, thereby securing pin 2054 to anvil assembly 2060. In the second position, clasping section 2022 is spaced apart from engagement section 2080 and pin 2054 is free to move away from anvil assembly 2060. Locking structure 2090 further includes a biasing member 2024, such as spring, for biasing clasping section 2022 toward the first position. Biasing member 2024 is disposed in a longitudinal slot 2026 formed on cam follower 2018. Longitudinal slot 2026 is configured to slidably receive a sliding pin 2028. Sliding pin 2028 is fixed to anvil assembly 2060 and, in conjunction with longitudinal slot 2026, directs the longitudinal motion of cam follower 218 through longitudinal opening 2062.

In operation, movement of pin 2054 distally toward anvil assembly 2060 forces cam follower 2018 slightly upwardly as engagement section forces its way past clasping section 2022, facilitated by the angled camming surface 2081 of engagement section 2080. Pin 2054 is advanced automatically upon approximation of the cartridge and anvil assemblies and/or in some embodiments manually until engagement section 2080 is positioned inside cavity 2094. Thus, this movement enables pin 2054 to slide under the hook portion of clasping section 2022 of clasp 2014 in a similar manner as described in the embodiment of FIG. 47. Clasp 2014 then returns to its first position of FIG. 58 to secure/retain pin 2054 after the engagement section passes by the clasping section 2022. While in the first position, clasping section 2022 engages engagement section 2080, maintaining pin 2054 secured to anvil assembly 2060 due to the abutment of the surfaces preventing proximal movement of pin 2054. The user can release pin 2054 from anvil assembly 2060 by rotating cam 2012 about pivot pin 2016. The rotary motion of cam 2012 causes clasping section 2022 to move to the second position (upwardly in the orientation shown) as seen in FIG. 59. When clasping section 2022 is located in the second position, the locking structure 2094 unlocks engagement section 2080 from anvil assembly 2060. Once engagement section 2080 has been unlocked, the pin 2054 can be moved proximally away from anvil assembly 2060 and the cartridge and anvil assemblies unapproximated. It should be appreciated that alternatively, to obtain the first position of clasp 2014, cam 2012 would be rotated to the position of FIG. 58. Various mechanisms can be used to rotate cam 2012.

The cam 2016 can optionally be provided with a series of teeth to engage a rack on cam 2012 to provide stepped (incremental) movement of the cam.

Figure 60:
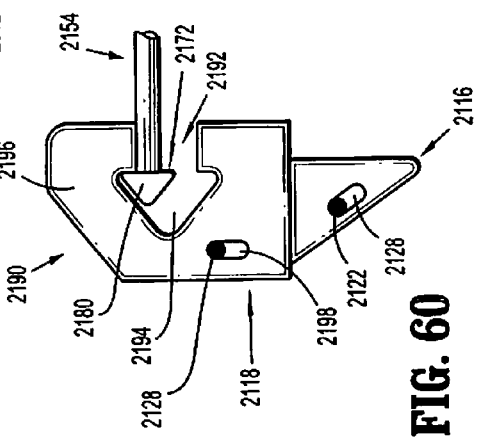

FIGS. 60 and 61 show another embodiment of a pin 2154 and a locking structure 2090 for use with a surgical stapling instrument such as instrument 100 of FIG. 1. In this embodiment, the surgical instrument includes a knife 2114 adapted to move longitudinally between a proximal position and a distal position. Pin 2154 includes an enlarged head engagement section 2180 disposed at a distal portion 2172 thereof. Engagement section 2180 has a tapered configuration and is configured to be securely received by locking structure 2190.

Locking structure 2190 is disposed in mechanical cooperation with an anvil assembly (not shown) and includes a first camming member 2116 and a second camming member 2118 operatively connected to each other. First camming member 2116 features a right triangular shape and is adapted to move transversely with respect to the anvil assembly (not shown) upon engagement with knife 2114. In addition, first camming member 2116 includes a diagonal slot 2120 configured to slidably receive a first pin 2122. First pin 2122 is fixed to the anvil assembly (not shown) and, during operation, guides the motion of first camming member 2116. In operation, first camming member 2116 moves from a first position, as seen in FIG. 60, to a second position, as shown in FIG. 61, upon engagement with knife 2114. While moving to the second position, first camming member 2116 drives second camming member 2118 from a first position, as depicted in FIG. 60, to a second position, as illustrated in FIG. 61. Second camming member 2118 includes an aperture 2192 for allowing passage of pin 2154, a catch 2196 configured to secured pin 2154 to the anvil assembly (not shown), and a slot 2198 adapted to slidably receive a second slidable pin 2128. Second slidable pin 2128 is fixed to the anvil assembly and, in conjunction with slot 2198, directs the longitudinal motion of second camming member 2118 during operation. Catch 2196 of second camming member 2118 includes cavity 2194 configured to receive engagement section 2180 of pin 2154.

In operation, pin 2154 is moved distally toward catch 2196 automatically upon approximation of the cartridge and anvil assemblies and/or in some embodiments manually while first and second camming members 2116, 2118 are in their respective second positions as shown in FIG. 61. During its distal translation, pin 2154 passes through aperture 2196 and positions itself inside cavity 2194 forcing camming member 2118 slightly upwardly (in the orientation of FIG. 60) so the pin can slide into the cavity. The angled surface of the engagement section 2180 facilitates such upward movement. First camming member 2116 is in its first position in FIG. 60. While first camming member 2116 is in its first position, second camming member 2118 is in its first position and catch 2196 engages engagement section 2180 of pin 2154, thereby locking pin 2154 to locking structure 2190. Pin 2154 is released from locking structure 2190 by translating knife 2114 distally toward first camming member 2118 (by actuation of a firing mechanism of the surgical stapler). When knife 2114 engages first camming member 2116, first camming member 2116 moves toward the second position and drives second camming member 2118 toward the second position as shown in FIG. 61 (see arrows). After second camming member 2118 has reached its second position, the user may remove pin 2154 from locking structure 2190 as the engagement section 2180 is spaced from the catch 2196. Retraction of knife 2114 allows the camming members to return to their normal position of FIG. 60.

While the above description contains many specifics, these specifics should not be construed as limitations on the scope of the present disclosure, but merely as illustrations of various embodiments thereof. Therefore, the above description should not be construed as limiting, but merely as exemplifications of various embodiments. Those skilled in the art will envision other modifications within the scope and spirit of the claims appended hereto.

What is claimed is:

1. A surgical instrument, comprising:
   a handle portion;
   an elongated portion defining a longitudinal axis and extending distally from the handle portion;
   an end effector disposed adjacent the elongated portion, the end effector including a first jaw member and a second jaw member, the first and second jaw members configured to clamp tissue therebetween;
   a pin disposed in mechanical cooperation with the first jaw member and including an engagement section, the pin being movable between a first position where the engagement section is spaced from the second jaw member and a second position where the engagement section of the pin engages the second jaw member, wherein the pin is rotatable from a first orientation to a second orientation, wherein the pin includes a protrusion extending radially therefrom and wherein the first jaw member includes a groove adapted to slidably receive the protrusion, the groove having a geometry adapted to cause the pin to rotate from the first orientation to the second orientation; and
   a locking structure disposed in the second jaw member, the locking structure being configured to secure the pin to the second jaw member to maintain a position of the second jaw member with respect to the first jaw member during actuation of the end effector.

2. The surgical instrument of claim 1, wherein the locking structure includes a cavity dimensioned to receive the pin, the cavity being adapted to retain the pin while the pin is positioned in the second orientation.

3. The surgical instrument of claim 2, wherein the second jaw member includes a bore leading to the cavity, the bore being dimensioned to receive the pin only while positioned in the first orientation.

4. The surgical instrument of claim 1, wherein the groove includes a straight portion and a curved portion, the curved portion being adapted to facilitate rotation of the pin between the first and second orientations.

\* \* \* \* \*